(12) United States Patent
Lu et al.

(10) Patent No.: US 9,011,816 B2
(45) Date of Patent: Apr. 21, 2015

(54) FIBRONECTIN TARGETING CONTRAST AGENT

(75) Inventors: Zheng-Rong Lu, Beachwood, OH (US); Xueming Wu, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 447 days.

(21) Appl. No.: 13/071,596

(22) Filed: Mar. 25, 2011

(65) Prior Publication Data

US 2012/0244070 A1    Sep. 27, 2012

(51) Int. Cl.
| | |
|---|---|
| A61K 51/00 | (2006.01) |
| A61M 36/14 | (2006.01) |
| A61K 49/14 | (2006.01) |
| A61K 49/12 | (2006.01) |
| A61K 51/06 | (2006.01) |
| A61K 51/08 | (2006.01) |

(52) U.S. Cl.
CPC ............... *A61K 49/14* (2013.01); *A61K 49/124* (2013.01); *A61K 51/065* (2013.01); *A61K 51/088* (2013.01)

(58) Field of Classification Search
CPC . A61K 51/008; A61K 2123/00; A61K 51/08; A61K 38/00; A61K 2120/00; A61K 51/00; A61K 51/0478; A61K 51/0485; A61K 51/04; A61K 51/065; A61K 51/088; A61K 49/14; A61K 49/124; C07F 13/005; C07F 5/003; C07F 5/00; C07F 17/00; C07C 45/77; C07C 49/92; C07C 51/412; C07C 51/41; C22B 60/0295; C01F 15/00; C08F 10/00; C07K 7/00; C07K 7/06; C07K 7/64; G01N 2458/00; G01N 2458/40

USPC .......... 424/1.11, 1.65, 1.69, 9.1, 9.2, 9.3, 9.4, 424/9.5, 9.6, 9.7, 9.8, 9.34, 9.341; 514/1, 514/1.1; 534/7, 10–16; 530/300, 317, 330
See application file for complete search history.

(56) References Cited

U.S. PATENT DOCUMENTS

| | | | | |
|---|---|---|---|---|
| 4,427,646 | A * | 1/1984 | Olexa et al. | ................. 424/1.69 |
| 5,344,639 | A | 9/1994 | Chiu et al. | |
| 7,238,341 | B2 * | 7/2007 | Zhang et al. | ................. 424/9.36 |
| 7,514,530 | B2 | 4/2009 | Divita et al. | |
| 7,597,895 | B2 | 10/2009 | Huang et al. | |
| 8,513,380 | B2 * | 8/2013 | Barker | ......................... 530/300 |
| 2010/0004316 | A1 | 1/2010 | Lu et al. | |

OTHER PUBLICATIONS

Tan et al, Biomacromolecules, 2010, vol. 11, No. 3, pp. 754-761.*
Tan, et al., An Effective Targeted Nanoglobular Manganese (II) Chelate Conjugate for Magnetic Resonance Molecular Imaging of Tumor Extracellular Matrix; Molecular Pharmaceutics, vol. 7, No. 4, pp. 936-943; Published on Web May 19, 2010, American Chemical Society.
Tan, et al., Peptide-Targeted Nanoglobular Gd-DOTA Monoamide Conjugates for Magnetic Resonance Cancer Molecular Imaging, Biomacromolecules 2010, 11, pp. 754-761, Published on Web Feb. 4, 2010; American Chemical Society.
Ye, et al., A Peptide Targeted Contrast Agent Specific to Fibrin-Fibronectin Complexes for Cancer Molecular Imaging with MRI; Bioconjugate Chem. 2008, 19, pp. 2300-2303, Published on Web Dec. 3, 2008; 2008 American Chemical Society.

* cited by examiner

*Primary Examiner* — Dameron Levest Jones
(74) *Attorney, Agent, or Firm* — Tarolli, Sundheim, Covell & Tummino LLP

(57) ABSTRACT

Example systems and methods enhance contrast in MRI images. To facilitate imaging of atherosclerotic plaques, arterial and venous, cardiac, and even tumor tissues and fibrosis, a fibrin-fibronectin complex or disease-related fibronectin specific MRI contrast agent (CLPD) has a specific binding affinity for fibronectin.

28 Claims, 2 Drawing Sheets

SEQUENCE LISTING

```
<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: cyclic peptide covalently attached to imaging
      agent (CLT1)

<400> SEQUENCE: 1

Cys Gly Leu Ile Ile Gln Lys Asn Glu Cys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: cyclic peptide covalently attached to imaging
      agent (CLT2)

<400> SEQUENCE: 2

Cys Asn Ala Gly Glu Ser Ser Lys Asn Cys
1               5                   10

<210> SEQ ID NO 3
<211> LENGTH: 5
<212> TYPE: PRT
<213> ORGANISM: Artificial Sequence
<220> FEATURE:
<223> OTHER INFORMATION: linear peptide covalently attached to imaging
      agent (CREKA)

<400> SEQUENCE: 3

Cys Arg Glu Lys Ala
1               5
```

FIBRONECTIN TARGETING CONTRAST AGENT

FEDERAL FUNDING NOTICE

The invention was developed with federal funding supplied under Federal Grant No.: NIH R01 CA097465 provided by the National Institute of Health. The Federal government has certain rights in the invention.

SEQUENCE LISTING

The instant application contains a Sequence Listing which has been submitted in ASCII format via EFS-Web and is hereby incorporated by reference in its entirety. Said ASCII copy, created on Sep. 9, 2013, is named Fibronectin Contrast Agent Sequences_ST25 and is 971 bytes in size.

BACKGROUND

Peptide multimeric contrast agents designed to bind to fibrin are described in Zhang, U.S. Pat. No. 7,238,341. Targeting peptides are described at the bottom of columns 35 and 36. However, binding to fibrin with conventional contrast agents developed in 2004 offers limited functionality.

In fact, currently the majority of imaging techniques offer limited functionality because they are invasive or have low spatial resolution. For example, conventional cancer imaging lacks target-specific contrast agents for accurate earlier diagnosis of malignant tumors. Furthermore, the results of the conventional cancer imaging are limited. MRI has improved spatial resolution that provides both anatomical and physiological information. However, MR images are only as useful as they are clear. Contrast agents are used to improve or increase the resolution of the image or to provide specific diagnostic information. Specifically, contrast agents detect cancer-related biomarkers and enhance the contrast of structures or fluids within the body in medical imaging.

To be effective, the contrast agent must interfere with the wavelength of electromagnetic radiation used in the imaging technique, alter the physical properties of tissue to yield an altered signal, or, as in the case of radiopharmaceuticals, provide the source of radiation itself. MRI and optical methods are unique among imaging modalities in that they yield complex signals that are sensitive to the chemical environment. While the signal from X-ray or radionuclide agents remains the same whether agents are free in plasma, bound to proteins or other targets, or trapped inside bone, certain contrast agents for MRI and optical imaging will have different signal characteristics in differing physiological environments. If the contrast agent is not sufficiently sensitive or present at high enough concentration, the signal changes may not be observed. If the signal changes are not observed the resulting MR images will be inaccurate or misleading, which may result in a misdiagnosis.

BRIEF DESCRIPTION OF THE DRAWINGS

The accompanying drawings, which are incorporated in and constitute a part of the specification, illustrate various example systems, methods, and other example embodiments of various aspects of the invention. Furthermore, elements may not be drawn to scale.

DEFINITIONS

Figure 1:
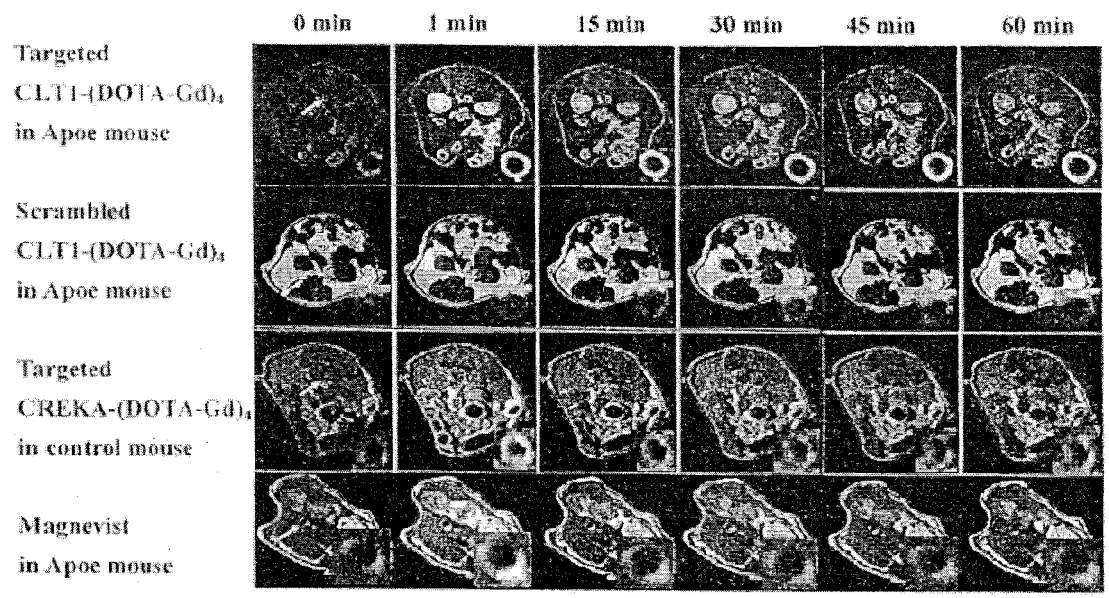
FIG. 1 illustrates in vivo MR images acquired in atherosclerotic Apo-E deficient mice.

For the purposes of this application, "DTPA" refers to a chemical compound comprising a substructure composed of diethylenetriaminepentaacetic acid, where the two primary amines are covalently attached to two acetic acid groups and the secondary amine has one acetic acid group covalently attached according to the following:

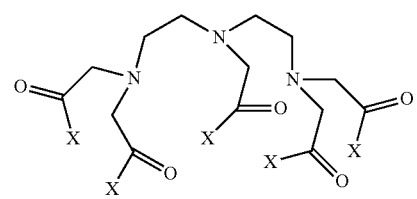

X is a heteroatom electron-donating group capable of coordinating a metal cation, preferably O$^-$, OH, NH$_2$, OPO$_3^{2-}$, or NHR, or OR where R is an aliphatic group. When an X group is tert-butoxy (tBu), the structure may be referred to as "DTPE" ("E" for ester).

For the purposes of this application, "DOTA" refers to a chemical compound comprising a substructure composed of 1,4,7,11-tetraazacyclododecanetetraacetic acid, where the amines have one acetic acid group covalently attached according to the following:

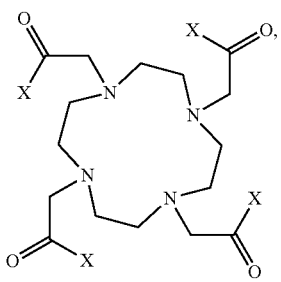

X is defined above.

For the purposes of this application, "NOTA" refers to a chemical compound comprising a substructure composed of 1,4,7-triazacyclononanetriacetic acid, where the amines have one acetic acid group or a substituted acetic acid group covalently attached according to the following:

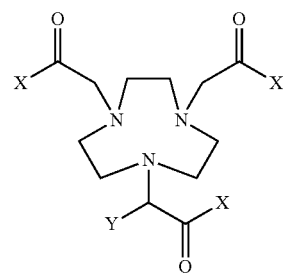

X is defined above. Y is H or $CH_2CH_2COZ$, where Z (not shown) is defined the same as X.

For the purposes of this application, "DO3A" refers to a chemical compound comprising a substructure composed of 1,4,7,11-tetraazacyclododecanetriacetic acid, where three of the four amines have one acetic acid group covalently attached and the other amine has a substituent with or without a functional group according to the following:

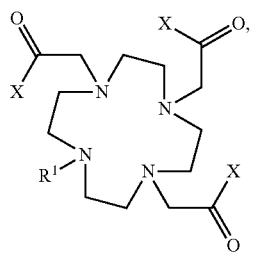

X is defined above and $R^1$ is a chemical moiety, preferably hydrogen, or an aliphatic, alkyl group, and cycloalkyl group with or without a functional group, preferably $O^-$, OH, $NH_2$, $OPO_3^{2-}$, or NHR, or OR where R is an aliphatic group. The preferred chelate "HP"-DO3A has $R^1$=—$CH_2$ (CHOH)$CH_3$.

The terms "chelating ligand," "chelating moiety," "chelator", and "chelate moiety" may be used to refer to a polydentate ligand which is capable of coordinating a metal ion, including DTPA (and DTPE), DOTA, DO3A, or NOTA molecule, or another suitable polydentate chelating ligand as is further defined herein, that is either coordinating a metal ion or is capable of doing so, either directly or after removal of protecting groups, or is a reagent, with or without suitable protecting groups, that is used in the synthesis of a contrast agent and comprises substantially all of the atoms that ultimately will coordinate the metal ion of the final metal complex. The term "chelate" refers to the actual metal-ligand complex, and it is understood that the polydentate ligand will eventually be coordinated to a medically useful metal ion.

The term "specific binding affinity" as used herein, refers to the capacity of a contrast agent to be taken up by, retained by, or bound to a particular biological component to a greater degree than other components. Contrast agents that have this property are said to be "targeted" to the "target" component. The compounds, contrast agents, and methods described herein relate to targeting fibronectin, fibronectin complexes, and oncofetal fibronectin. Contrast agents that lack this property are said to be "non-specific" or "non-targeted" agents.

The term "relaxivity" as used herein, refers to the increase in either of the MRI quantities $1/T_1$ or $1/T_2$ per millimolar (mmol) concentration of paramagnetic ion or contrast agent, which quantities may be different if the contrast agent contains a multiplicity of paramagnetic ions, where $T_1$ is the longitudinal or spin-lattice, relaxation time, and $T_2$ is the transverse or spin-spin relaxation time of water protons or other imaging or spectroscopic nuclei, including protons found in molecules other than water. Relaxivity is expressed in units of $mM^{-1} s^{-1}$.

The term "open coordination site" as used herein refers to a site on a metal ion that is generally occupied by a water or solvent molecule.

As used herein, the term "peptide" refers to a chain of amino acids that is about 2 to about 75 amino acids in length (e.g., 3 to 50 amino acids).

The terms "target binding" and "binding" for purposes herein refer to non-covalent interactions of a contrast agent with a target. These non-covalent interactions are independent from one another and may be, inter alia, hydrophobic, hydrophilic, dipole-dipole pi-stacking, hydrogen bonding, electrostatic associations, or Lewis acid-base interactions.

The term "capping moiety" refers to a chelate, organic dye, contrast agent, or stabilizing moiety. Suitable stabilizing moieties are biologically inert.

To the extent that the term "includes" or "including" is employed in the detailed description or the claims, it is intended to be inclusive in a manner similar to the term "comprising" as that term is interpreted when employed as a transitional word in a claim.

As used herein, a plurality of items, structural elements, compositional elements, and/or materials may be presented in a common list for convenience. However, these lists should be construed as though members of the list are individually identified as a separate and unique member. Thus, no individual member of a list should be construed as a de facto equivalent of another member of the same list solely based on their presentation in a common group without indications to the contrary.

Concentrations, amounts, and other numerical data may be expressed or presented in a range format. It is to be understood that a range format is used merely for convenience and brevity and thus should be interpreted flexibly to include not only the numerical values explicitly recited as the limits of the range, but also to include the individual numerical values or sub-ranges encompassed within the ranges as if numerical values and sub-ranges are explicitly recited.

DETAILED DESCRIPTION

Fibronectins are structural glycoproteins that form insoluble extracellular matrix via complexation with other extracellular matrix components, including collagen and fibrin. Oncofetal fibronectin, which has an extradomain A (EDA), B (EDB) or type III domain, is a cancer-related isoform of fibronectin expressed in malignant tumors. Clinical evidence indicates that the oncofetal fibronectin in the extracellular matrix plays a biological role in the aggressiveness of cancer cells. It is also expressed around the vasculature in the tumor tissues to promote tumor angiogenesis. Fibronectin is also expressed in atherosclerotic plaques and fibrotic tissues. Fibronectin and its complexes with fibrin or collagen are the targets for the targeted MRI contrast agents for imaging cancer, atherosclerotic plaques, and fibrosis. Thus, unlike Zhang, example compounds facilitate fibronectin specific processes, methods, and images.

Described herein are imaging agents that have specific binding affinity for fibronectin and its complexes with fibrin or collagen. The imaging agents have a cyclic peptide covalently attached to an imaging agent. The peptide includes the sequence CGLIIQKNEC SEQ ID NO 1 (CLT1), CNAGESSKNC SEQ ID NO: 2 (CLT2), or a linear peptide comprising the sequence CREKA SEQ ID NO: 3 (CREKA).

Example compounds, contrast agents, and methods enhance contrast in MRI images for the early detection of maladies (e.g., atherosclerotic plaques and tumors). To facilitate imaging of atherosclerotic plaques, arterial and venous, cardiac, and even tumor tissues and fibrosis, a fibrin-fibronectin complex or disease-related fibronectin specific MRI contrast agent (CLPD) has a specific binding affinity for fibronectin.

The imaging agent includes a chelating agent and a metal ion. The chelating agent generally possesses one or more groups capable of forming a covalent bond with the peptide. A number of different chelating agents known in the art can be used herein. In one aspect, the chelating agent comprises an acyclic or cyclic compound comprising at least one heteroatom (e.g., oxygen, nitrogen, sulfur, phosphorous) that has lone-pair electrons capable of coordinating with the imaging agent. An example of an acyclic chelating agent includes ethylenediaminetetraacetate (EDTA) and its derivatives, diethylenetriaminepentaacetate (DTPA) or its derivatives. Examples of cyclic chelating agents include 1,4,7,10-tetraazadodecanetetraacetate (DOTA) and its derivatives, 1,4,7,10-tetraazadodecane-1,4,7-triacetate (DO3A) and its derivatives, 1,4,7,10-tetraazacyclotridecanetetraacetic acid (TRITA) and its derivatives, 1,4,8,11-tetraazacyclotetradecane-1,4,8,11-tetraacetic acid (TETA) and its derivatives, 1,4,7,10-tetraazadodecanetetramethylacetate (DOTMA) and its derivatives, 1,4,7,10-tetraazadodecane-1,4,7-trimethylacetate (DO3MA) and its derivatives, N,N',N'',N'''-tetraphosphonatomethyl-1,4,7,10-tetraazacyclododecane (DOTP) and its derivatives, 1,4,7,10-tetraazacyclododecane-1,4,7,10-tetrakis(methylene methylphosphonic acid) (DOTMP) and its derivatives, 1,4,7,10-tetraazacyclododecane-1,4,7,10-tetrakis(methylene phenylphosphonic acid) (DOTPP) and its derivatives, or 1,4,7-triazacyclononanetriacetic acid (NOTA) and its derivatives. The term "derivative" is defined herein as the corresponding salt and ester thereof of the chelating agent.

The selection of the metal ion can vary depending upon the detection technique (e.g., MRI, PET, etc.). In one aspect, metal ions useful in magnetic resonance imaging include $Gd^{+3}$, $Eu^{+3}$, $Tm^{+3}$, $Dy^{+3}$, $Yb^{+3}$, $Mn^{+2}$, or $Fe^{+3}$ ions. In another aspect, ions useful in PET and SPECT imaging include $^{55}Co$, $^{64}Cu$, $^{67}Cu$, $^{47}Sc$, $^{66}Ga$, $^{68}Ga$, $^{90}Y$, $^{97}Ru$, $^{99m}Tc$, $^{111}In$, $^{109}Pd$, $^{153}Sm$, $^{177}Lu$, $^{186}Re$, $^{188}Re$. In another aspect, the imaging agent comprises an MRI agent, where the MRI agent comprises a chelating agent and a metal ion comprising $Gd^{+3}$, $Eu^{+3}$, $Tm^{+3}$, $Dy^{+3}$, $Yb^{+3}$, $Mn^{+2}$, or $Fe^{+3}$ ions. In a further aspect, the imaging agent comprises $Gd^{+3}$ chelated to diethylenetriaminepentaacetate (DTPA) and the peptide is SEQ ID NO 1.

Compounds described herein can exist or be converted to a pharmaceutically acceptable salt. The salts can be prepared by treating the free acid with an appropriate amount of a chemically or pharmaceutically acceptable base. Representative chemically or pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. (e.g. at room temperature). The molar ratio of the compound to base used is chosen to provide the ratio desired for particular salts. For preparing, for example, the ammonium salts of the free acid starting material, the starting material can be treated with approximately one equivalent of base to yield a salt.

If the compounds possess carboxylic acid groups, these groups can be converted to pharmaceutically acceptable esters using techniques known in the art. Alternatively, if an ester is present on the compound, the ester can be converted to a pharmaceutically acceptable ester using transesterification techniques.

Pharmaceutical compositions composed of the imaging agents described herein can be formulated in excipients the biological system or entity can tolerate. Examples of excipients include, but are not limited to, water, saline, Ringer's solution, dextrose solution, Hank's solution, and other aqueous physiologically balanced salt solutions. Nonaqueous vehicles (e.g., fixed oils, vegetable oil, olive oil, sesame oil, triglycerides, propylene glycol, polyethylene glycol), and injectable organic esters (e.g, ethyl oleate) can also be used. Other useful formulations include suspensions containing viscosity-enhancing agents (e.g., as sodium carboxymethyl-cellulose, sorbitol, dextran). Excipients can also contain minor amounts of additives (e.g., substances that enhance isotonicity and chemical stability). Examples of buffers include phosphate buffer, bicarbonate buffer and Tris buffer, while examples of preservatives include thimerosol, cresols, formalin and benzyl alcohol.

The imaging agents described herein can be used to image a tissue in a subject. In one aspect, the method comprises (1) administering to the subject an imaging agent described herein, and (2) detecting the imaging agent. In one aspect, the imaging agents described herein can be used to image cancer cells and tumors. Examples of different types of cancers include, but are not limited to, breast cancer, liver cancer, stomach cancer, colon cancer, pancreatic cancer, ovarian cancer, lung cancer, kidney cancer, brain cancer, prostate cancer, testicular cancer, glioblastoma, sarcoma, bone cancer, head-and-neck cancers, and skin cancer. The agents can also be used in detecting wounds and atherosclerotic plaques.

Complexes between gadolinium(III) or manganese(II) and other paramagnetic ions and organic ligands are widely used to enhance and improve MRI contrast. Paramagnetic agents enable this contrast to be increased. Paramagnetic agents modify the $T_1$ and $T_2$ of the nuclei of the tissues where they are accumulated and hence the intensity of the signal emitted by these tissues. The signals emitted by the tissue yield anatomical information. Furthermore, functional information can be determined by observing the accumulation of the paramagnetic contrast agent. Targeting fibronectin and its complexes (e.g. fibrin, collagen) with paramagnetic ions provides significant imaging and diagnostic information.

The paramagnetic ions may include gadolinium(III). Gadolinium(III) complexes increase contrast by increasing the nuclear magnetic relaxation rates of protons found in the water molecules that are accessible to the contrast agents during MRI. The relaxation rate of the protons in these water molecules increases relative to protons in other water molecules that are not accessible to the contrast agent. This change in relaxation rate leads to improved contrast of the images. In addition, this increase in relaxivity within a specific population of water molecule protons can result in an ability to collect more image data in a given amount of time. This in turn results in an improved signal to noise ratio. Therefore, targeting fibronectin and its complexes with fibrin or collagen minimizes spurious background imaging signals. Four Gd-DOTA moieties of CLPD provide a significant relaxation enhancement effect that allows CLPD to further enhance MR molecular imaging of fibrin-fibronectin complexes in tumor tissue.

The imaging agents described herein can be used to detect the presence of fibronectin or fibrin-fibronectin complexes in the angiogenic tumor tissues. The correlation of fibronectin or fibrin-fibronectin complexes to tumor angiogenesis may provide an effective method for tumor angiogenesis imaging with MRI. Accurate assessment of tumor angiogenesis is involved in tumor grading, assessment of tumor response to anticancer therapies, particularly antiangiogenesis therapies, and patient management.

Fibronectin and fibrin-fibronectin complexes are also present in the plasma clots of wounds and other pathologic tissues with leaky blood vessels (e.g., atherosclerotic plaques). Fibronectin plays a prominent role in hemostasis and wound healing. Fibrinogen is activated to form insoluble fibrin clot following vascular injury. The clot also serves as a provisional matrix for adhesion and migration of cells or proteins including fibronectin, which is incorporated into the fibrin clot upon fibrin polymerization. Thus, the imaging agents described herein can be used to image vascular integrity and assess wound healing, atherosclerosis and tumor response to antiangiogenesis therapies.

Techniques for detecting the imaging agent once incorporated into the cells or tissue are known in the art. For example, magnetic resonance imaging (MRI), positron emission tomography (PET), single photon emission computed tomography (SPECT) and optical cameras can be used to detect the imaging agent. Additionally, the imaging agents described herein can be useful in a variety of other medical procedures, including, but not limited to, angiography, plethysmography, lymphography, mammography, cancer diagnosis, and functional and dynamic MRI.

The imaging agents described herein are useful in evaluating the performance of bioactive agents (e.g., drugs). In one aspect, a method for evaluating the ability of a bioactive agent to reduce the size of a tumor or to prevent the tumor from growing comprises: imaging the tumor with an imaging agent described herein and measuring the size of the tumor; administering the bioactive agent in a sufficient amount to the subject to reduce the size of the tumor or prevent the growth of the tumor; re-imaging the tumor with an imaging agent described herein and measuring the size of the tumor, and comparing the size of tumor after administration of the bioactive agent to the size of the tumor prior to administration of the bioactive agent.

In another aspect, a method for evaluating the ability of a bioactive agent to prevent or reduce plaque growth in one or more blood vessels in a subject comprises: imaging the blood vessels with an imaging agent and measuring the presence and amount of plaques; administering the bioactive agent in a sufficient amount to the subject to reduce or prevent plaque formation; re-imaging the blood vessels with an imaging agent described herein and measure the presence and amount of plaques, and comparing the amount of plaques after administration of the bioactive agent to the amount of plaques prior to administration of the bioactive agent.

These methods generally involve administering a bioactive agent having a certain therapeutic property and evaluating its performance by comparing a tumor, plaque, or other tissue that can be imaged with the imaging agents described herein prior to and after administration of the bioactive agent.

In addition to accumulating specifically in tumor cells, the imaging agents are readily excreted from the subject. The term "substantially all of the imaging agent is excreted from the subject" is defined herein as the ability not to detect the imaging agent in the blood of the subject by a detection means, for example, magnetic resonance after administration to the subject.

It is understood that given particular aspects of the disclosed compositions and methods can be compared to the specific examples and embodiments disclosed herein. By performing this comparison, the relative efficacy of particular embodiments can be determined. Preferred compositions and methods are disclosed in the Examples herein, and it is understood that these compositions and methods, while not necessarily limiting, can be performed with the compositions and methods disclosed herein.

Conjugating CLTI peptide (CGLIIQKNEC) (SEQ ID NO: 1) to Gd(III) chelates result in targeted contrast agent for targeted tumor MR imaging. CLTI peptide binds to fibrin-fibrinectin complexes or oncofetal fibronectin in the stroma of solid tumors. Since cancer-related fibronectin or fibrin-fibronectin complexes are abundantly present in tumor stroma, sufficient amounts of the targeted contrast agents can bind to the tumor tissue, resulting in agents with improved relaxivities in strong tumor enhancement for MR cancer molecular imaging.

Standard solid-phase peptide synthesis was employed to synthesize peptide CLT1 (CGLIIQKNEC) (SEQ ID NO: 1) from Fmoc-protected amino acids on a 2-chlorotrityl chloride resin. At the end of the peptide synthesis, a short linker, Fmoc-12-amino-4,7,10-trioxadodecanoic acid (532 mg, 1.2 mmol) in DMF was reacted with the peptide (960 mg, 0.4 mmol) on the beads under the presence of HOBt (162 mg, 1.2 mmol), PyBop (624 mg, 1.2 mmol) and excess DIPEA at room temperature for 1 hour. After removing the Fmoc group with piperidine DMF solution, propargyl-dPEG1-NHS ester (270 mg, 1.2 mmol), HOBt (162 mg, 1.2 mmol), PyBop (624 mg, 1.2 mmol) and DfPEA in DMF were added and reacted at room temperature for 1 hour to conjugate propargyl group at the N-terminal of the peptide. The peptide-PEG-propargyl conjugate was then cleaved from the resin using trifluoroacetic acid solution containing 2.5% ethane-1,2-dithiol, 2.5% water, and 1.0% triisobutylsilane. The product was exposed to air to allow the formation of disulfide bonds for the cyclic peptide.

Example 1

Synthesis of Cys-Gly-Leu-Ile-Ile-Gln-Lys-Asn-Glu-Cys (CLT1) (SEQ ID NO: 1)

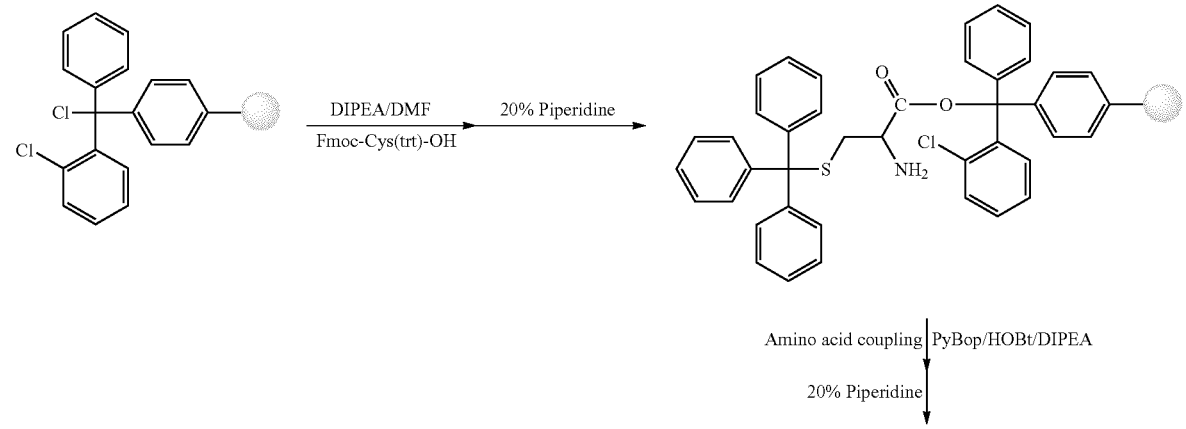

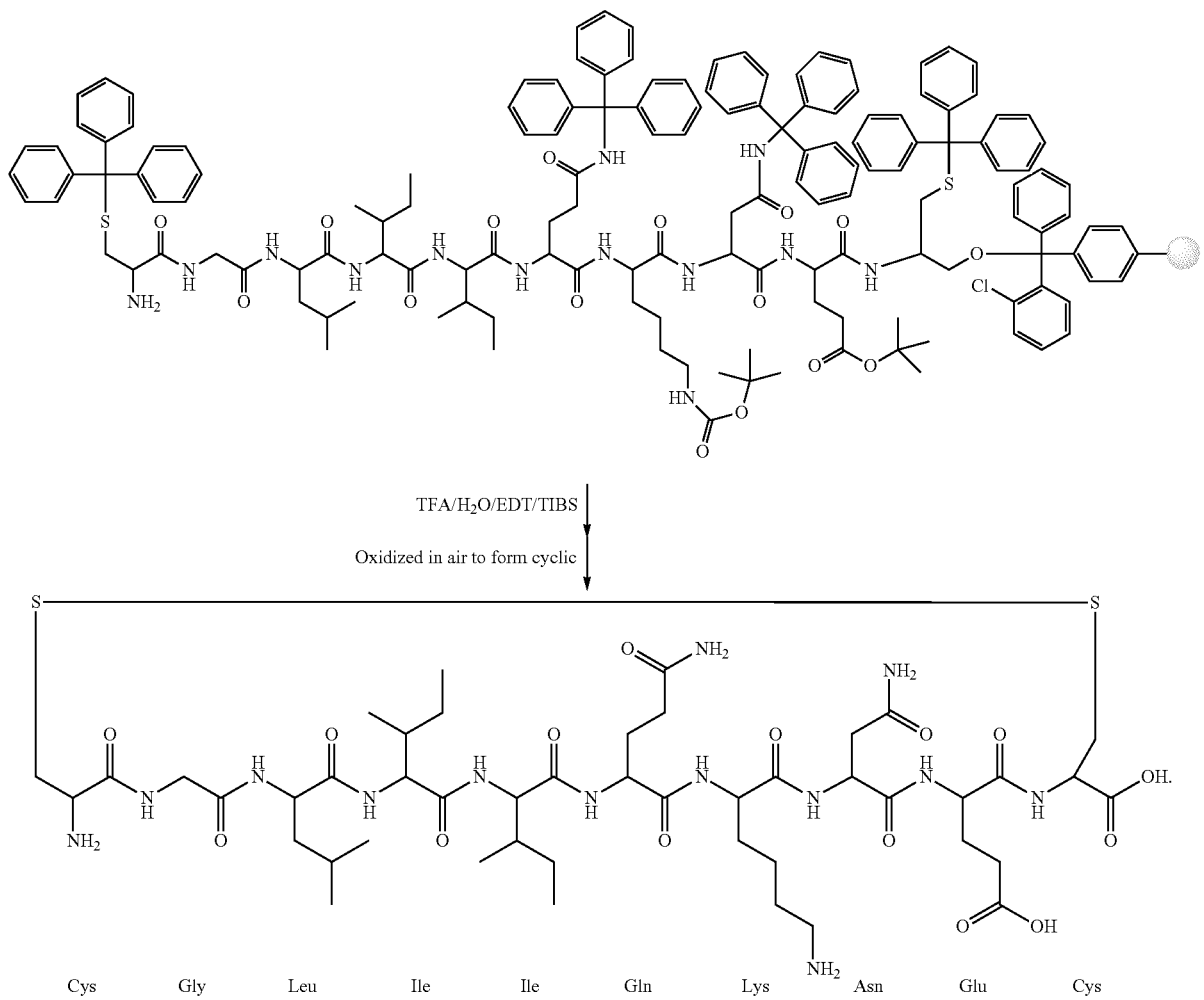

Cys Gly Leu Ile Ile Gln Lys Asn Glu Cys (SEQ ID NO: 1)

The peptide, CLT1, was synthesized using solid phase peptide synthesis (SPPS). 2-Chlorotrityl chloride resin (1.27 g, 2 mmol, loading rate=1.58 mmol Cl/g) was suspended and swollen in anhydrous dichloromethane (DCM) (10 mL) and shaken for one hour in an ISOLUTE column. The resin was then filtered and extensively washed with DCM and anhydrous dimethylformamide (DMF) (3×20 mL). A mixture of Fmoc-Cys(trt)-OH (586 mg, 1 mmol) and N,N-diisopropylethylamine (DIPEA) (800 µL) in 10 mL DMF was added to the resin, and the suspension was shaken for two hours.

The solution was then drained, and the resin was washed with DCM/DMF three times. The resin was further shaken with methanol (10 mL) and DIPEA (800 µL) for twenty minutes to block the remaining active chloride on the resin. After washing with DCM and DMF, the Fmoc protecting group was removed with 20% piperidine in DMF; the removal took place for five minutes, three times.

Fmoc-Glu(OtBu)-OH (1.28 g, 3 mmol, 3 times excess) and PyBop/HoBt/DIPEA (1560 mg/405 mg/800 µL, 3 times excess) in DMF (10 mL) were added to the resin containing primary amine and shaken for 50 minutes. The resin was subjected to a washing cycle. The Fmoc protecting group was removed with 20% piperidine in DMF; the removal took place for five minutes, three times. Aspargine, lysine, glutamine, isoleucine, isoleucine, leucine, glycine, cysteine residues were sequentially incorporated by reacting the resin three times excess using 3 mmol for: Fmoc-Asn(trt)-OH, Fmoc-Lys(Boc)-OH, Fmoc-Lln(trt)-OH, Fmoc-Ile-OH, Fmoc-Leu-OH, Fmoc-Gly-OH, Fmoc-Cys(trt)-OH and PyBop/HoBt/DIPEA (three times excess) in DMF, followed by removal of Fmoc protecting groups.

The quality of coupling reactions involving primary amino groups was monitored with the Kaiser test. After a cycle, the resin was washed and dried under reduced pressure before proceeding to the next reaction. After finishing the reactions, a portion of the resin was taken to be suspended in a cocktail of 10 mL trifluoroacetic acid, 94 mL water, 2.5 mL ethane-1,2-dithiol, and 5 mL triisobutylsilane. The portion of resin and the cocktail were shaken for ten hours at room temperature. The solution was dropped to cold ethyl ether (200 mL) and a solid precipitated. The mixture was vortexed for five minutes and centrifuged for three minutes. The mixture was then washed with ether four times and dried under reduced pressure to yield compound CLT1.

Example 2
Synthesis of Dendrimeric CLT1-PEG-(Lys)$_3$-(DOTA-Gd)$_4$
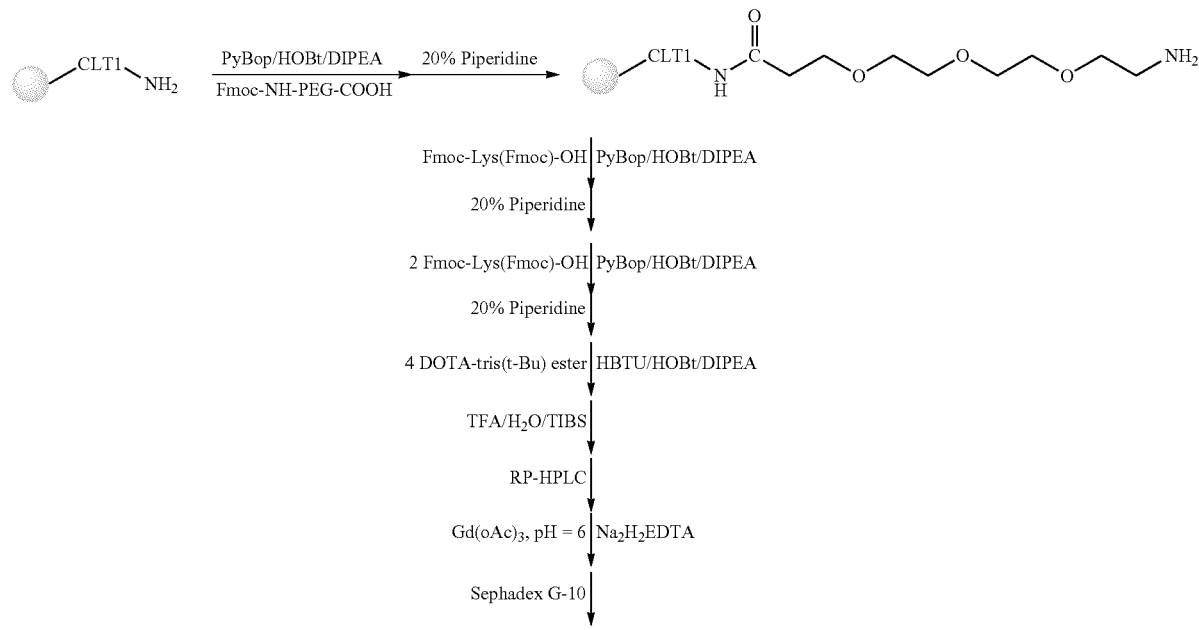
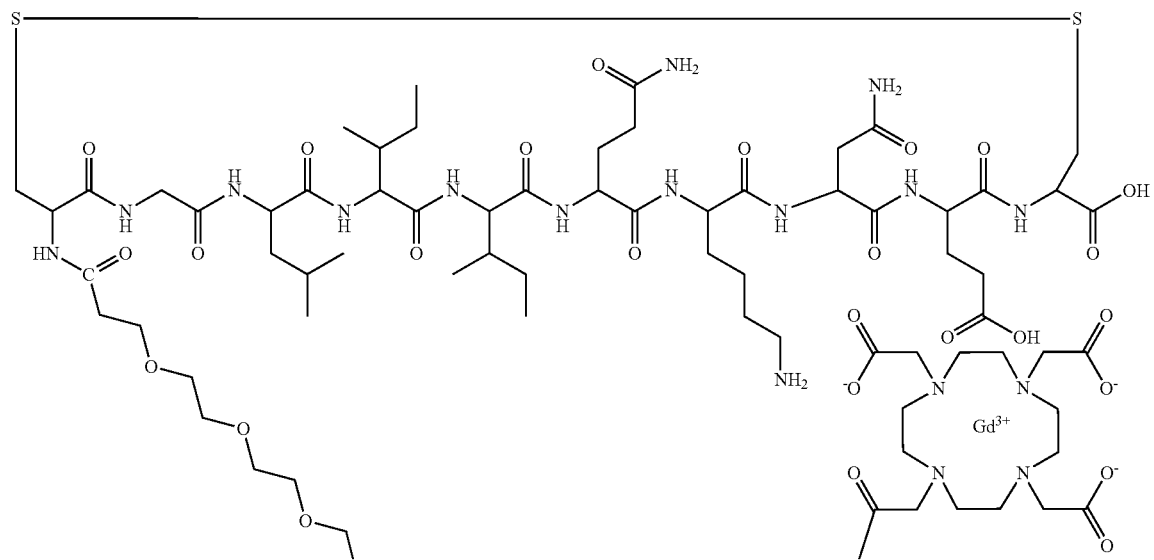

-continued

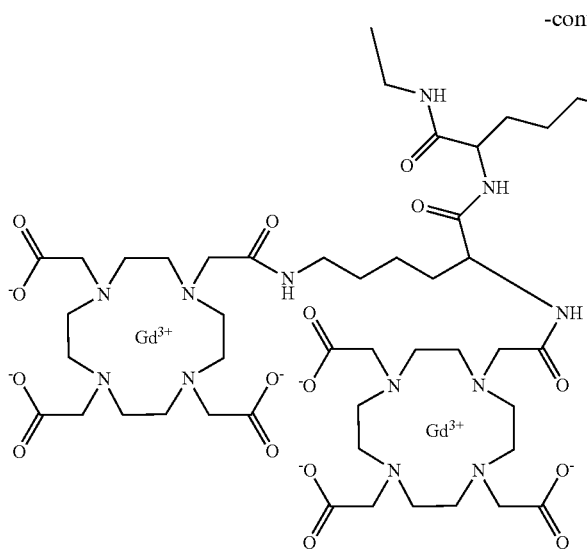
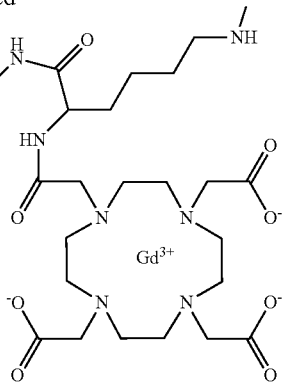

In a similar manner in which cysteine, glutamic acid, aspargine, lysine, glutamine, isoleucine, isoleucine, leucine, glycine and cysteine residues were sequentially incorporated to produce CLT1, here PEG, lysine, 2 lysines are sequentially incorporated by reacting the resin. The resin containing CLT1 is reacted with three times excess of Fmoc-NH-PEG-COOH (3 mmol), Fmoc-Lys(Fmoc)-OH (3 mmol), Fmoc-Lys (Fmoc)-OH (6 mmol), and PyBop/HoBt/DIPEA (three times in excess) in DMF. DOTA groups were incorporated by reacting the resin with DOTA-tris(t-Bu) ester (6.87 g, 12 mmol, three times excess) in the presence of PyBop/HoBt/DIPEA in DMF for two hours.

The resin was then suspended in a cocktail of 10 mL trifluoroacetic acid (TFA), 94 mL of water, 2.5 mL thane-1, 2-dithiol (EDT), and 5 mL triisobutylsilane (TIBS) and shaken for ten hours at room temperature. The solution was placed in 200 mL of cold ethyl ether and a solid precipitated. The mixture was vortexed for five minutes and centrifuged for three minutes. The mixture was washed with ether four times and dried under reduced pressure to yield the compound 2(CLT1-(PEG)$_2$-(Lys)$_3$-(DOTA)$_4$).

The ligand 2 (0.4 mmol) was dissolved in 30 mL of water. The pH was adjusted to 6 with 1 N sodium hydroxide. Gadolinium acetate tetrahydrate (Gd(OAc)$_3$.4H$_2$O) (0.98 g, 2.4 mmol, one and half excess) was added to the ligand solution. The reaction was stirred for forty-eight hours at room temperature. Residual free Gd$^{3+}$ was entrapped with EDTA (5 mL, 1 mmol). The reaction was stirred for 30 minutes. The product was isolated from solution and purified by reverse phase HPLC.

Example 3

Synthesis of Dendrimeric CREKA-PEG-(Lys)$_3$-(DOTA-Gd)$_4$

In a similar manner in which alanine, lysine, glutamic acid, arginine, and cysteine residues were sequentially incorporated to produce CREKA, here PEG, lysine, 2 lysines are sequentially incorporated by reacting the resin. NH$_2$-PEG-COOH and lysine dendrimer was conjugated to the peptide on the resin, followed by conjugation of DOTA complexation with Gd(III).

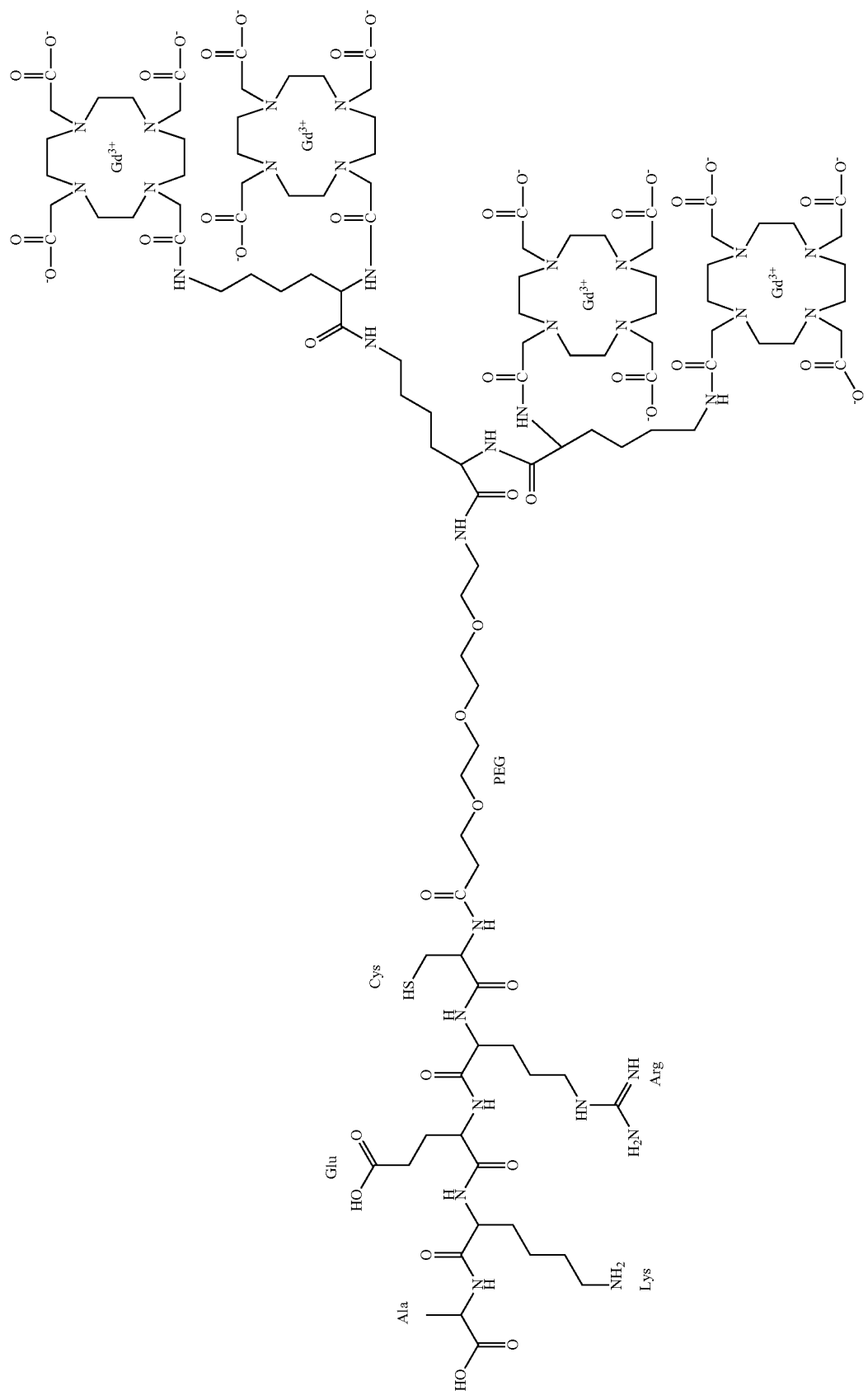

Example 4

Synthesis of Linear CREKA-PEG-(Lys)$_3$-(DOTA-Gd)$_4$

The peptide of Cys-Arg-Glu-Lys-Ala (CREKA) (SEQ ID NO: 3) was synthesized in a similar manner as above using solid-phase synthesis. PEG, Lysine, Lysine, Lysine were then sequentially incorporated to CREKA with 3 times excess of Fmoc-NH-(PEG)$_2$-COOH, Fmoc-Lys(ivDde)-OH, Fmoc-Lys(ivDde)-OH and Fmoc-Lys(Fmoc)-OH in the presence of PyBop/HoBt/DIPEA in DMF. After the ivDde protection groups were removed by 2% hydrazine in DMF, DOTA groups were incorporated by reacting the resin with DOTA-tris(t-Bu) ester in the presence of PyBop/HoBt/DIPEA in DMF for 2 h. The final resin was then suspended in a cocktail of trifluoroacetic acid (TFA), water (H$_2$O), ethane-1,2-dithiol (EDT), and triisobutylsilane (TIS) (94/2.5/2.5/1) and shaken for 6 hours at room temperature. The solution was dropped to cold ethyl ether (200 ml) and a solid precipitated. The mixture was vortexed for 5 min and centrifuged for 3 min, washed with ether 4 times, dried under reduced pressure, and purified by reverse phase HPLC to give compound 2 (CREKA-(PEG)$_2$-(Lys)$_3$-(DOTA)$_4$). MALDI-TOF-MS: m/z 2738.65 [M+H]$^+$.

The ligand CREKA-(PEG)$_2$-(Lys)$_3$-(DOTA)$_4$ (0.4 mmol) was dissolved in water (30 ml). pH was adjusted to 6 with 1 N sodium hydroxide. Gadolinium acetate tetrahydrate (Gd (oAc)$_3$.4H$_2$O) (0.98 g, 2.4 mmol, 1.5 times excess) was added to the ligand solution. The reaction was stirred for 48 h at room temperature. Residual free Gd$^{3+}$ was entrapped with ethylenediaminetetraacetic acid (EDTA) (5 ml, 1 mmol). A reducing agent tris(2-carboxyethyl)phosphine (TCEP) was added to prevent free thiol groups to be oxidized during the reaction. The reaction was stirred for 30 min. The crude product is then purified by Sephadex G-10 column to give final product compound 3 (CREKA-(PEG)$_2$-(Lys)$_3$-(DOTA-Gd)$_4$). MALDI-TOF-MS: m/z 3355.71 [M+H]$^+$.

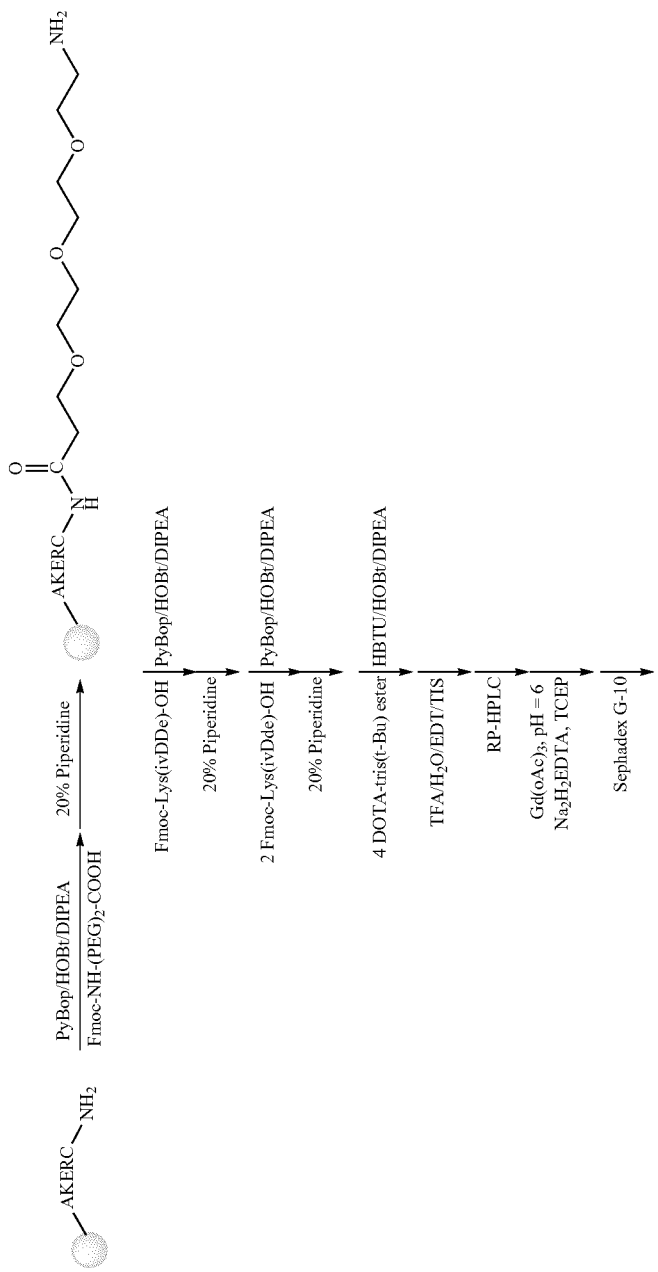

-continued
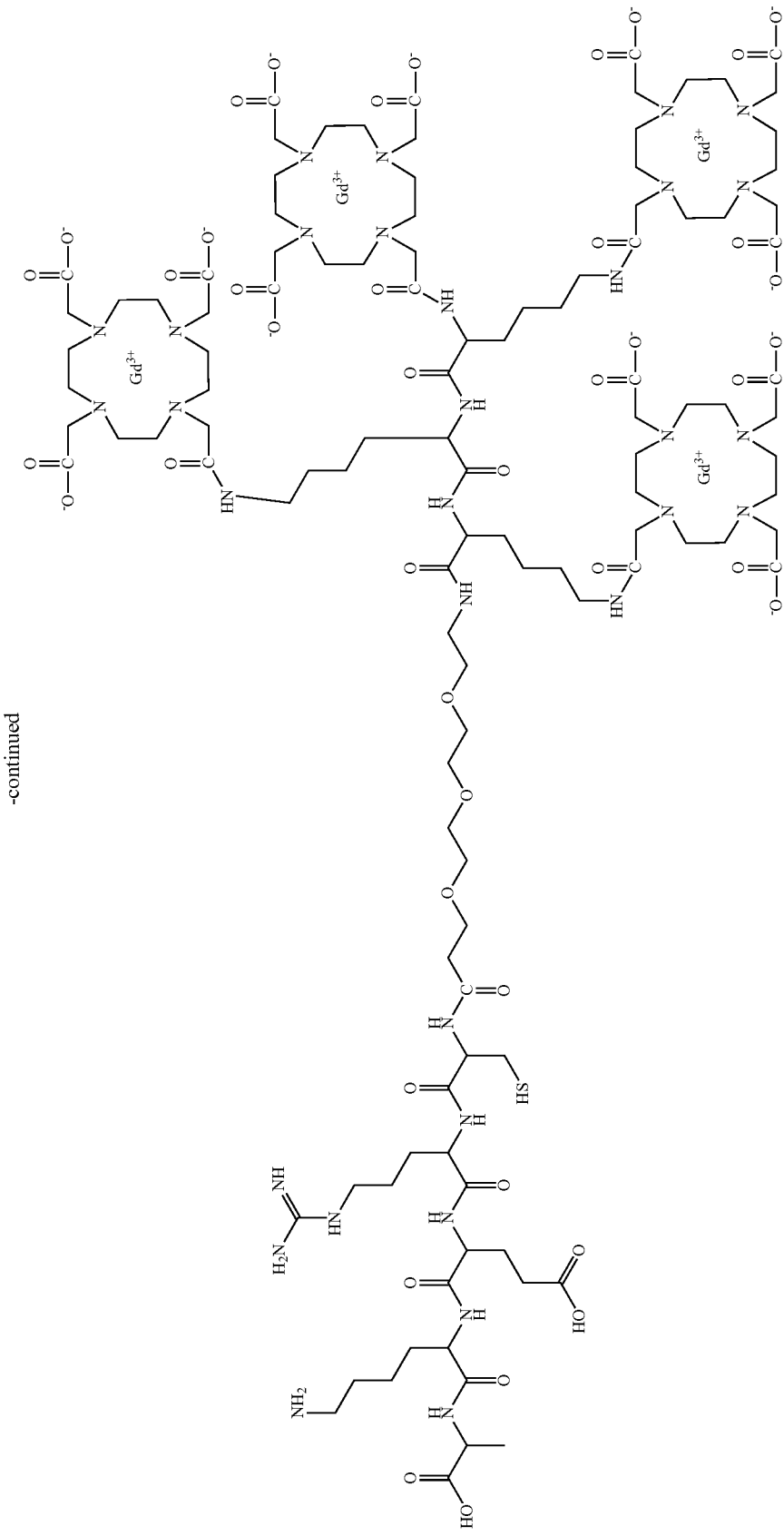

Example 5
Synthesis of CLT1-PEG-(Lys)$_4$-(DOTA-Gd)$_4$-FITC
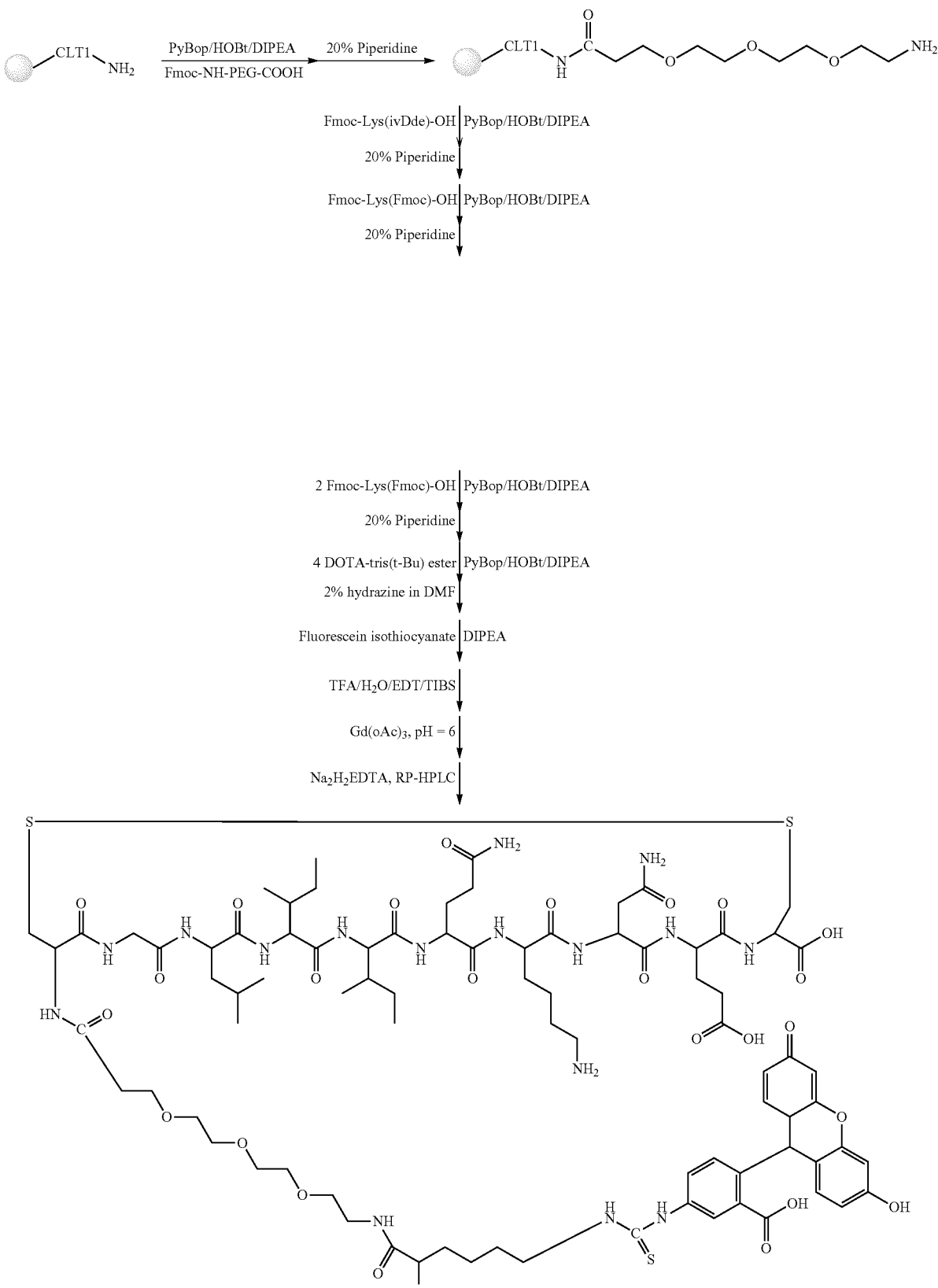

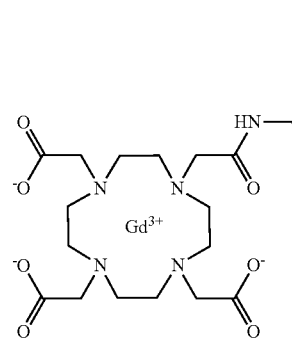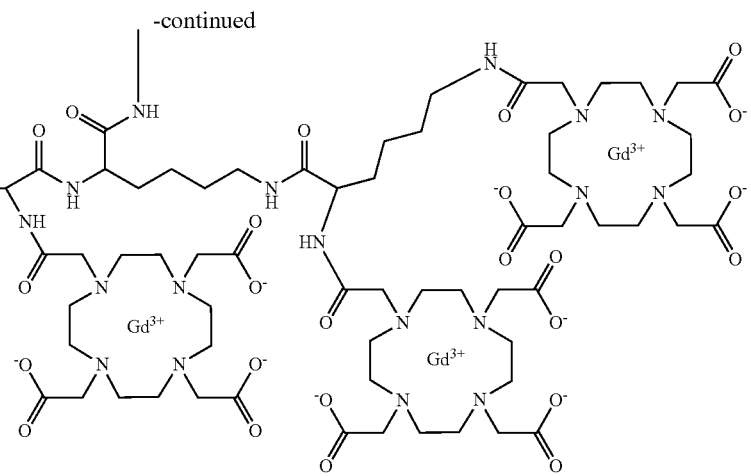

-continued

Lysine can be incorporated with CLT1 by reacting the resin containing the CLT1 with 3 times excess of Fmoc-NH-$(PEG)_2$-COOH (3 mmol), Fmoc-Lys-(ivDde)-OH (3 mmol), Fmoc-Lys(Fmoc)-OH (3 mmol), Fmoc-Lys(Fmoc)-OH (6 mmol), and PyBop/HoBt/DIPEA (in three times excess) in DMF.

DOTA groups were incorporated by reacting the resin with DOTA-tris(t-Bu) ester (68.7 g, 12 mmol, three times excess) in the presence of PyBop/HoBt/DIPEA in DMF for 2 hours. After washing with DCM/DMF the ivDde protecting group was removed with 2% hydrasine monohydratein DMF (for ten minutes, six times). Then, fluorescein isothiocyanate (FITC, 1.17 mg, 3 mmol, three times excess) and DIPEA (100 µL) in DMF (10 mL) were added to the resin and shaken for six hours at room temperature. The ISOLUTE column was wrapped in aluminum foil during the reaction to protect it from light.

The final resin was then suspended in a cocktail of trifluoroacetic acid, water, ethane-1,2-dithol, and triisobutylsilane (10 mL, 94 mL, 2.5 mL, 2 mL, 5 mL, and 1 mL) and was shaken for ten hours at room temperature. The ISOLUTE column was wrapped in aluminum during the reaction, to protect the reaction from light. The solution was dropped to cold ethyl ether (200 mL) and a solid precipitated. The mixture was vortexed for 5 minutes and centrifuged for 3 minutes. The mixture was washed with ether four times, and dried under reduced pressure to give the compound: 3(CLT1-$(PEG)_2$-Lys)$_4$-(DOTA)$_4$-FITC). ESI-MS: m/z 1886.1 $[M+2H]^{2+}$, 1257.7 $[M=3H]^{3+}$, 943.6 $[M=4H]^{4+}$, 755.3 $[M+5H]^{5+}$.

The ligand 3 (0.4 mmol) was dissolved in water (30 mL). The pH of the mixture was adjusted to 6 with 1 N sodium hydroxide. Gadolinium acetate tetrahydrate $(Gd(OAc)_3.4H_2O)$ (0.98 g, 2.4 mmol, one and half times excess) was added to the ligand solution. The reaction was stirred for 48 hours at room temperature. Residual free $Gd^{3+}$ was entrapped with EDTA (5 mL, 1 mmol). The reaction was stirred for 30 minutes. The reaction solution was protected from light by wrapping in aluminum foil during process. The final product was isolated from solution and purified by reverse phase HPLC in a dark room.

Models

In animal tumor models female athymic nu/nu mice (4-6 weeks old), were purchased from the Animal Resource Center (ARC) of Case Western Universitey. A suspension of PC3 with GFP cells (PC3-GFP) were harvested and suspended in a sterile phosphate-buffered saline solution. The mixture ($5\times10^5$ cells, 25 µL) was surgically inoculated into the ventral prostate through the dorsal prostate.

A human breast tumor model was also run. A 4T1 cell line was cultured using ATCC complete growth medium. Female Balb/c mice (4-6 weeks old) were purchased from Jackson Lab. The suspension of 4T1 cells in PBS was mixed with Matrigel matrix at 1:1 ratio. The mixture ($2\times10^6$ cells, 100 µL) was surgically implanted in the mammary pad of a mouse when a mouse was approximately 8-10 weeks old.

An atherosclerotic mice model was run with 12 week old Apoe knockout mice (B6.129P2 Apotem1UNC/J) and control mice (C57BL/J6) were purchased from Jackson Lab. Apoe knockout mice were fed with a high fat diet (60% fat) after arriving and were maintained for 6 months. Control mice were fed with a normal diet (6% fat).

When tumor sizes reached 0.5-1.0 cm in diameter in 3-4 weeks, Texas red labeled peptides were intravenously injected into tumor bearing mice at a dose of 30 nmol per mouse. At two hours after injection, the mice were sacrificed, and the tumors and major organs were collected and imaged immediately on a Maestro Flourescence Imaging instrument.

Results

FIG. 1 illustrates in vivo MR images acquired in atherosclerotic ApoE-deficient mice before and after injection of targeted CLTI-(DOTA-Gd)$_4$ or CREKA-(DOTA-Gd)$_4$ and non-targeted controls. Arrows point to atherosclerotic aorta and insets are enlargements of aorta. The images show a baseline image at zero minutes before an injection of contrast agent. The images progress to injection and in fifteen minute intervals up to sixty minutes. The images illustrate targeted peptides, scrambled peptides, and Magnevist. The targeted peptides resulted in greater and longer enhancement in tumor tissue compared to non-targeted scrambled peptides and controls.

Figure 2:
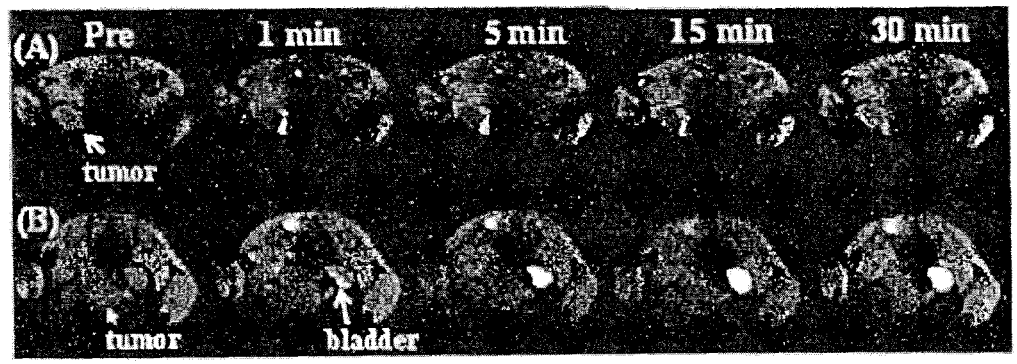
FIG. 2 illustrates in vivo MR images of orthotopic breast cancer tumors in mice.

FIG. 2 illustrates T1-weighted axial 2D gradient images of subcutaneous breast cancer tumor. Both CLT1-(DOTA-Gd)$_4$ and non-targeted scrambled CLT1-(DOTA-Gd)$_4$ were investigated in male BALB/c mice bearing orthotopic 4T1 human breast tumor. FIG. 2 shows the T1 weighted axial 2D gradient tumor images for targeted and non-targeted agents at 0.03 mmol-Gd/kg. The images in row (A) of the targeted CLT1-(DOTA-Gd)$_4$. Images in row (A) illustrate a time sequence of the targeted CLT1-(DOTA-Gd)$_4$. Images in row (B) illustrate the time sequence for non-targeted CLT1-(DOTA-Gd)$_4$. The targeted CLT1-(DOTA-Gd)$_4$ resulted in greater and longer enhancement in tumor tissue compared to non-targeted scrambled CLT1-(DOTA-Gd)$_4$.

Figure 3:
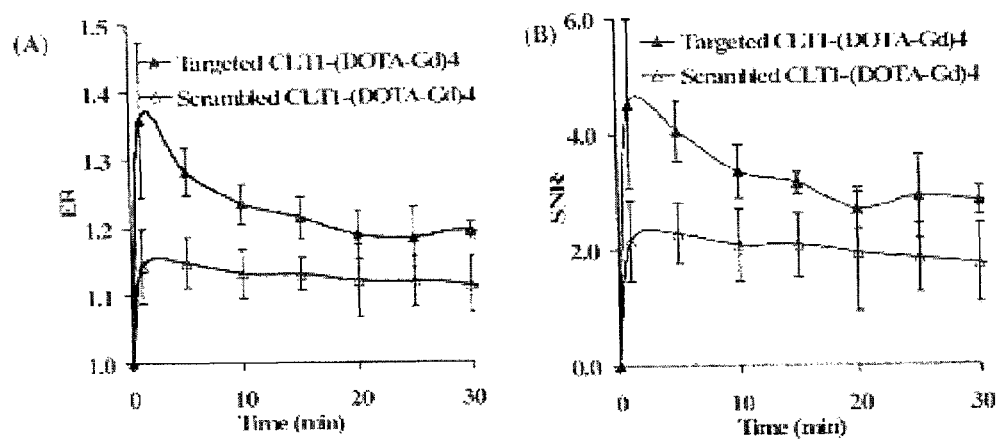
FIG. 3 illustrates an enhancement ratio and a signal to noise ratio of the targeted CLT1-(DOTA-Gd)$_4$ and non-targeted scrambled CLT1-(DOTA-Gd)$_4$.

FIG. 3 illustrates an enhancement ratio and a signal to noise ratio of the targeted CLT1-(DOTA-Gd)$_4$ and non-targeted scrambled CLT1-(DOTA-Gd)$_4$. The MRI contrast agents, targeted CLT1-(DOTA-Gd)$_4$ and non-targeted scrambled CLT1-(DOTA-Gd)$_4$ were administer at 0.03 mmol-Gd/kg in nu/nu nude athymic mice (n=4) bearing orthotopic human prostate tumor. Signal intensity within the tumor tissue showed that the targeted agents at 0.03 mmol-Gd/kg resulted in greater enhancement than non-target agents.

What is claimed is:

1. A compound according to formula I:

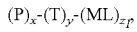

where P is a peptide comprising peptide sequence SEQ ID NO: 1, SEQ ID NO: 2, or SEQ ID NO: 3 that binds to fibronectin, T is a monomer that forms a dendrimer or an oligomer, L is a ligand that conjugates to the functional groups of the dendrimer or oligomer and complexes with a metal ion M, wherein x is a value within a range of 1 to 10, y is a value within a range of 1 to 63, and where z is a value within a range of 1 to 64, and a spacer between the dendrimer or oligomer and the peptide, or a pharmaceutically acceptable salt or ester thereof.

2. The compound of claim 1, wherein the spacer is a polyethyleneglycol spacer.

3. The compound of claim 1, where L is selected from the group consisting of ethylenediamine, diethylenetriaminepentaacetate (DTPA), 1,4,7,10-tetraazadodecanetetraacetate (DOTA), 1,4,7,10-tetraazadodecane-1,4,7-triacetate (DO3A), ethylenediaminetetraacetate (EDTA), 1,4,7,10-tetraazacyclotridecanetetraacetic acid (TRITA), 1,4,8,11-tetraazacyclotetradecane-1,4,8,11-tetraacetic acid (TETA), 1,4,7,10-tetraazadodecanetetramethylacetate (DOTMA), 1,4,7,10-tetraazadodecane-1,4,7-trimethylacetate (DO3MA), N,N',N'',N'''-tetraphosphonatomethyl-1,4,7,10-tetraazacyclododecane (DOTP), 1,4,7,10-tetraazacyclododecane-1,4,7,10-tetrakis (methylene methylphosphonic acid) (DOTMP), 1,4,7,10-tetraazacyclododecane-1,4,7,10-tetrakis (methylene phenylphosphonic acid) (DOTPP), 1,4,7-triazacyclononanetriacetic acid (NOTA), and N,N'-ethylenedi-L-cysteine.

4. The compound of claim 1, where M is a metal ion selected from the group consisting of $Gd^{+3}$, $Eu^{+3}$, $Tm^{+3}$, $Dy^{+3}$, $Yb^{+3}$, $Mn^{+2}$, $Fe^{+3}$, $^{55}Co$, $^{64}Cu$, $^{64}Cu$, $^{47}Sc$, $^{66}Ga$, $^{68}Ga$, $^{90}Y$, $^{97}Ru$, $^{99m}Tc$, $^{111}In$, $^{109}Pd$, $^{153}Sm$, $^{177}Lu$, $^{186}Re$, and $^{188}Re$.

5. The compound of claim 1, where M is a PET or SPECT imaging agent, where the agent comprises $^{55}Co$, $^{64}Cu$, $^{67}Cu$, $^{47}Sc$, $^{66}Ga$, $^{68}Ga$, $^{90}Y$, $^{97}Ru$, $^{99m}Tc$, $^{111}In$, $^{109}Pd$, $^{153}Sm$, $^{177}Lu$, $^{186}Re$, or $^{188}Re$ coordinated to a chelating agent.

6. The compound of claim 1, where M is an MRI agent, comprising a chelating agent and a metal ion selected from the group consisting of $Gd^{+3}$, $Eu^{+3}$, $Tm^{+3}$, $Dy^{+3}$, $Yb^{+3}$, $Mn^{+2}$, and $Fe^{+3}$ ions.

7. The compound of claim 1, where the compound is a pharmaceutically acceptable salt or ester.

8. A compound according to formula II or a pharmaceutically acceptable salt or ester thereof:

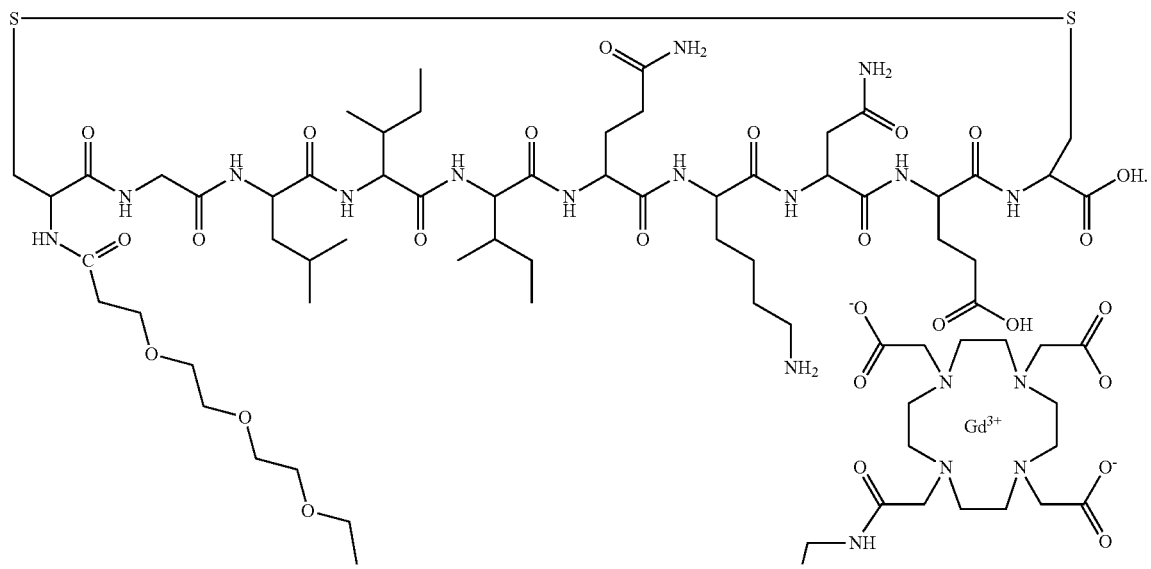

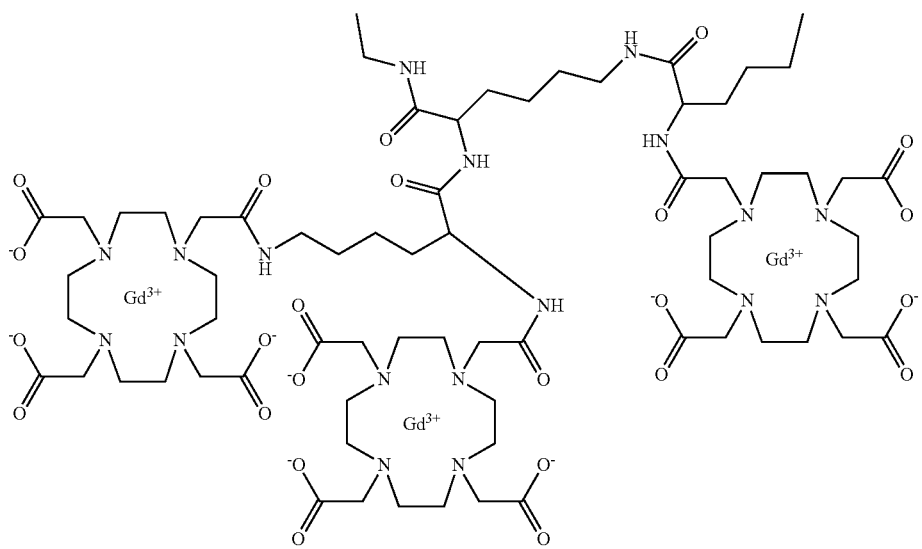

9. The compound of claim 8, where the compound is a pharmaceutically acceptable salt or ester.

10. A compound according to formula III or a pharmaceutically acceptable salt or ester thereof:

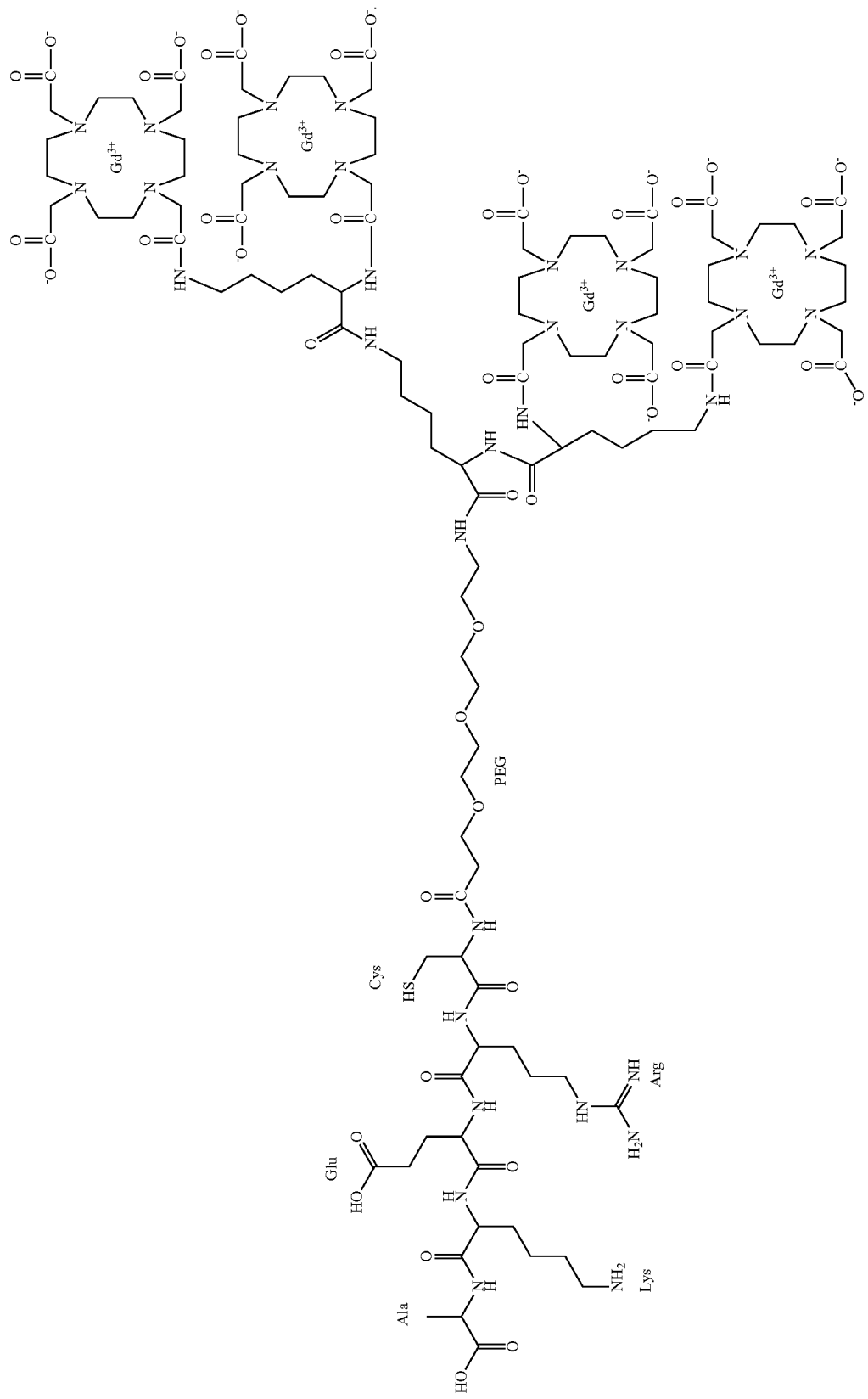

11. The compound of claim 10, where the compound is a pharmaceutically acceptable salt or ester.

12. A compound according to formula IV or a pharmaceutically acceptable salt or ester thereof:

IV
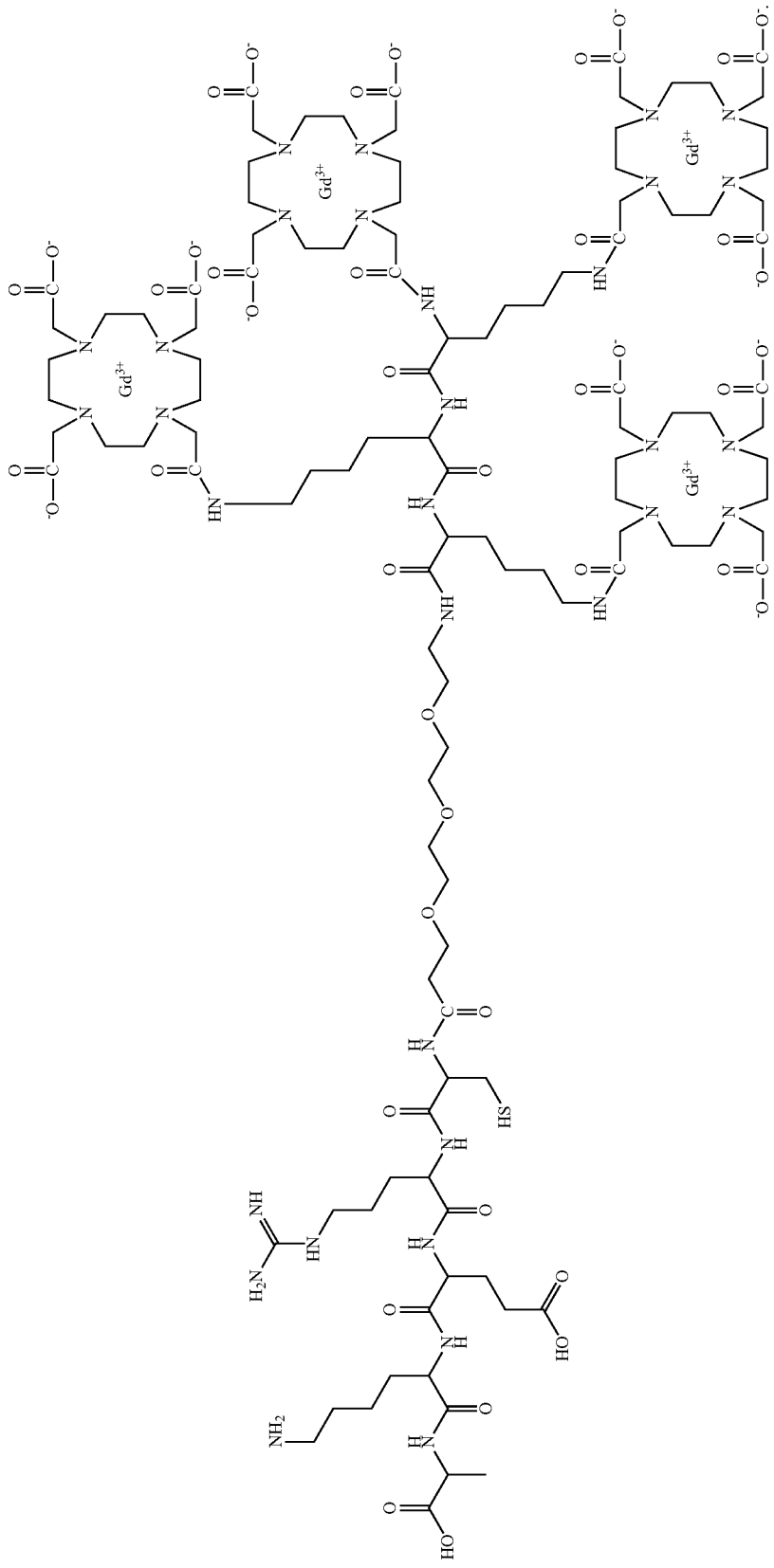

13. The compound of claim 12, where the compound is a pharmaceutically acceptable salt or ester.

14. A compound according to formula V or a pharmaceutically acceptable salt or ester thereof:

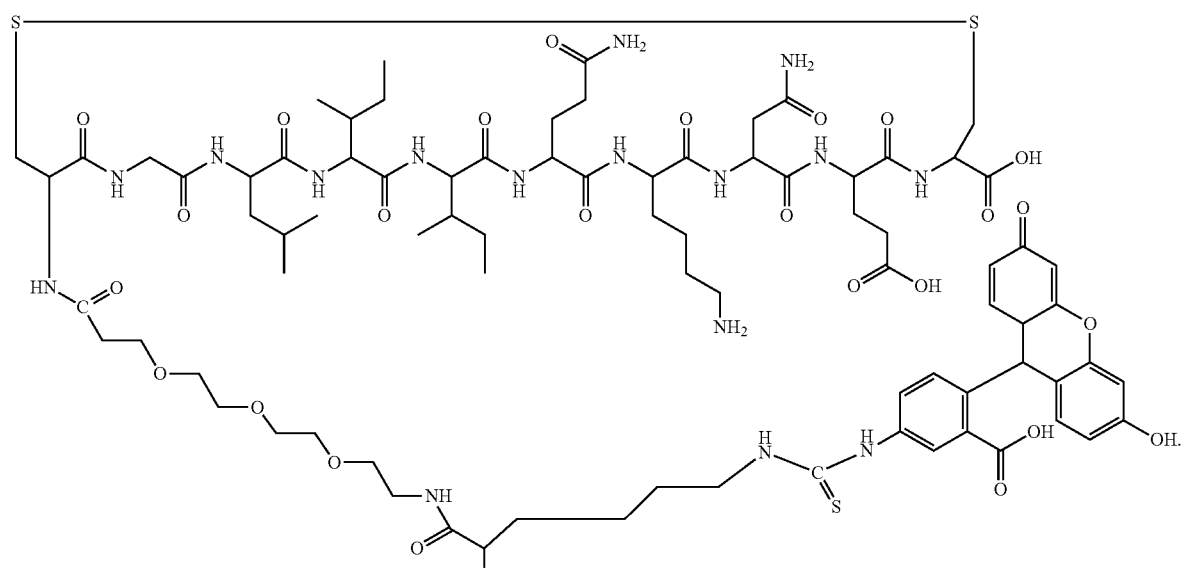

V

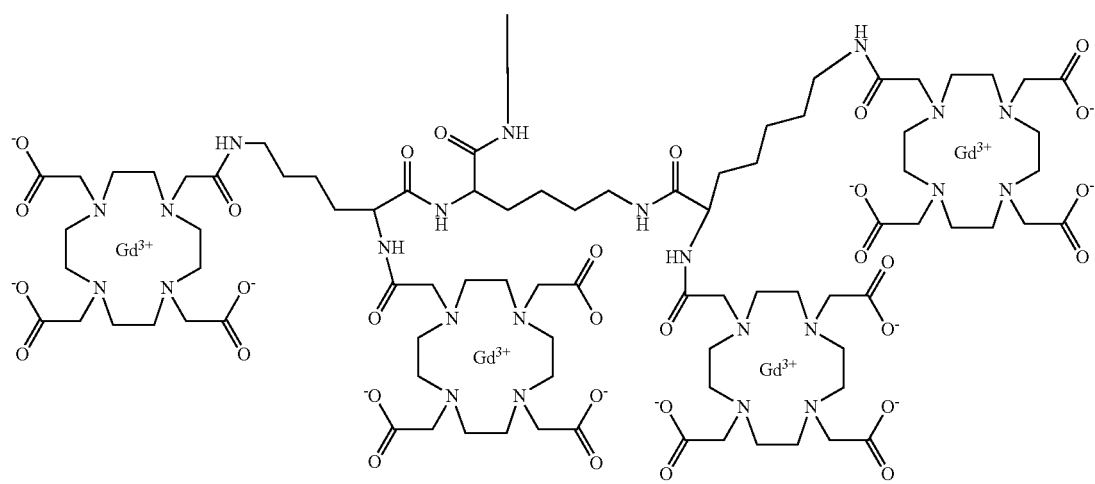

15. The compound of claim 14, where the compound is a pharmaceutically acceptable salt or ester.

16. A method of imaging a tissue in a subject, comprising:
administering an effective amount of a polypeptide-based contrast agent to the subject;
allowing time for the contrast agent to reach the tissue; and
imaging the tissue that has been contacted by the polypeptide-based contrast agent,
wherein the polypeptide-based contrast agent is a compound according to formula II,

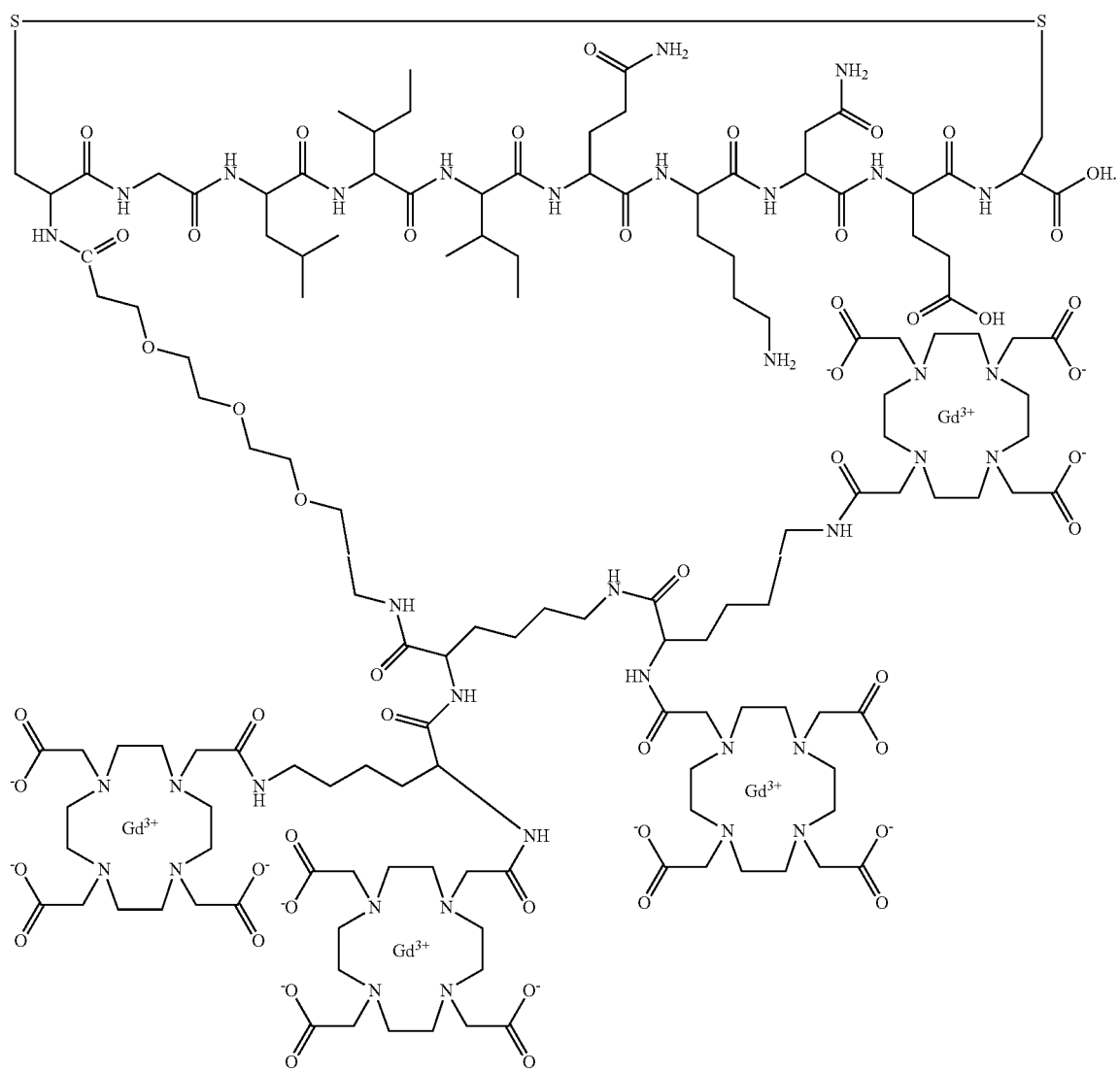

17. The method of claim 16, wherein the step of imaging the tissue uses a signal selected from the group consisting of an MR signal, a SPECT signal, a ICP-OES signal, a laser light scattering signal, and a PET signal.

18. The method of claim 16, where the tissue comprises one or more glycoproteins selected from the group consisting of fibronectin, a fibrin-fibronectin complex, and oncofetal fibronectin.

19. A method imaging a tissue in a subject, comprising:
administering an effective amount of a polypeptide-based contrast agent to the subject;
allowing time for the contrast agent to reach the tissue; and
imaging the tissue that has been contacted by the polypeptide-based contrast agent,
wherein the polypeptide-based contrast agent is a compound according to formula III,

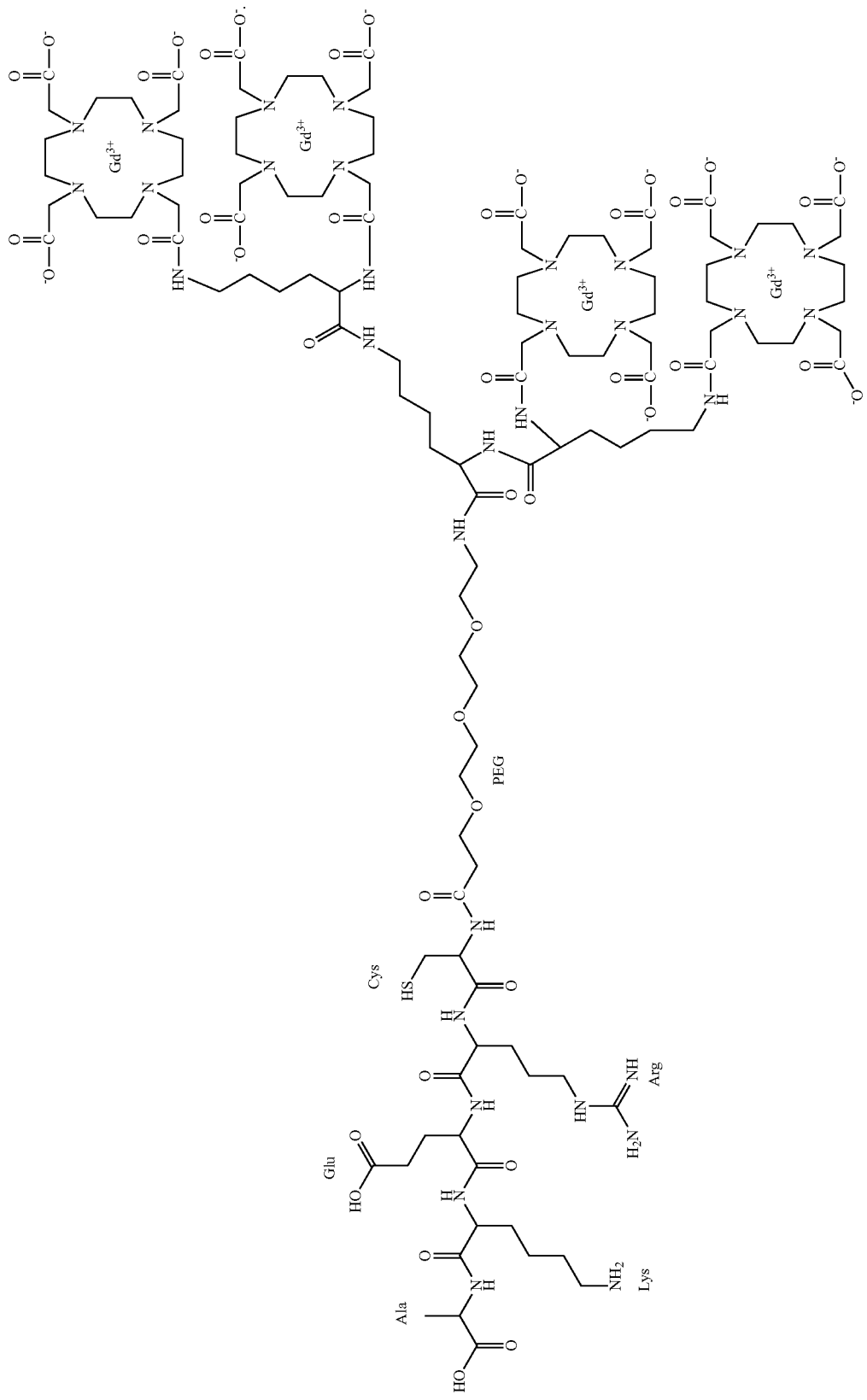

20. The method of claim 19, wherein the step of imaging the tissue uses a signal selected from the group consisting of an MR signal, a SPECT signal, a ICP-OES signal, a laser light scattering signal, and a PET signal.

21. The method of claim 19, where the tissue comprises one or more glycoproteins selected from the group consisting of fibronectin, a fibrin-fibronectin complex, and oncofetal fibronectin.

22. A method of imaging tissue in a subject, comprising:
administering an effective amount of a polypeptide-based contrast agent to the subject;
allowing time for the contrast agent to reach the tissue; and
imaging the tissue that has been contacted by the polypeptide-based contrast agent,
wherein the polypeptide-based contrast agent is a compound according to formula IV, IV
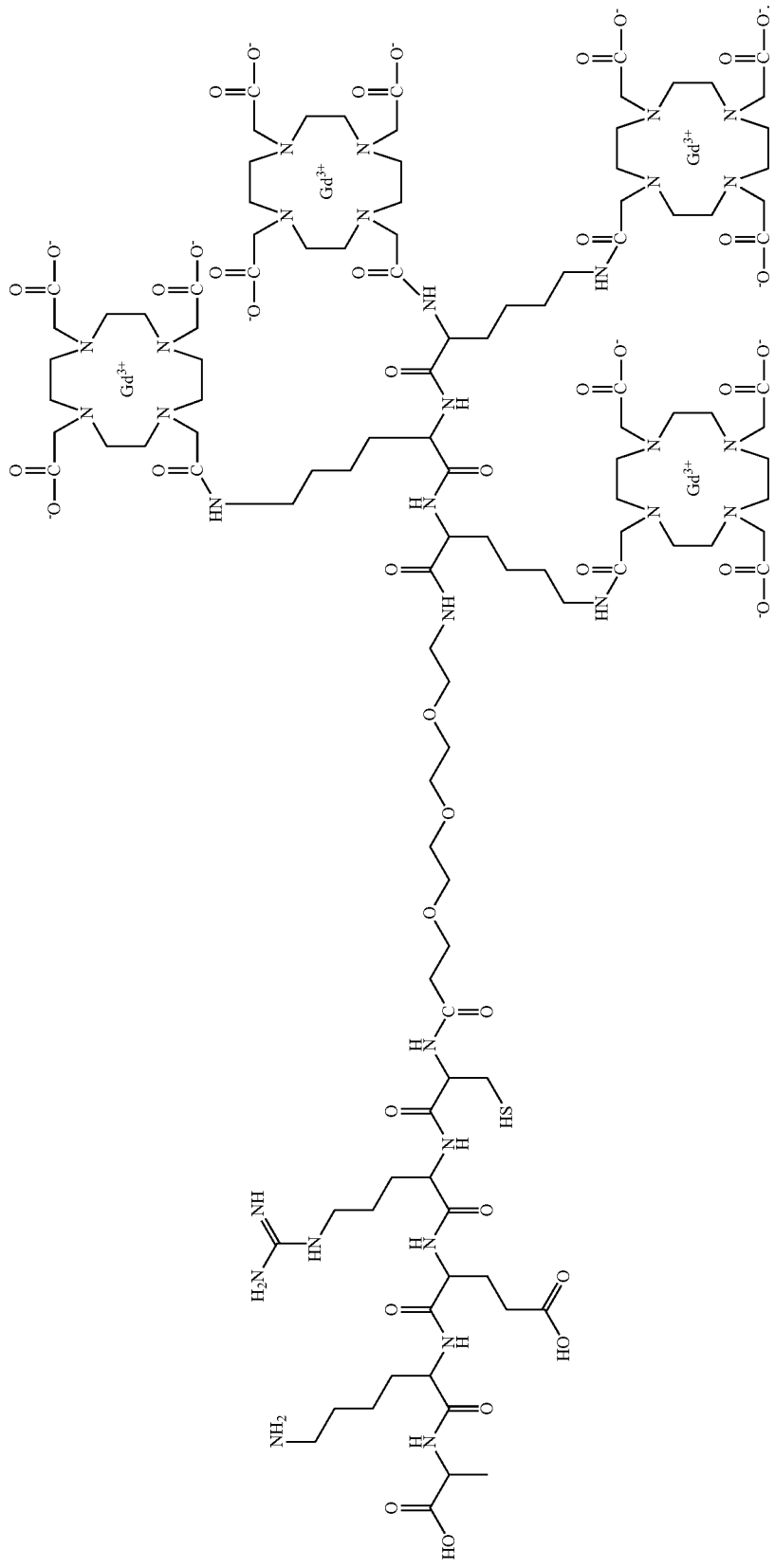

23. The method of claim 22, wherein the step of imaging the tissue uses a signal selected from the group consisting of an MR signal, a SPECT signal, a ICP-OES signal, a laser light scattering signal, and a PET signal.

imaging the tissue that has been contacted by the polypeptide-based contrast agent, wherein the polypeptide-based contrast agent is a compound according to formula V,

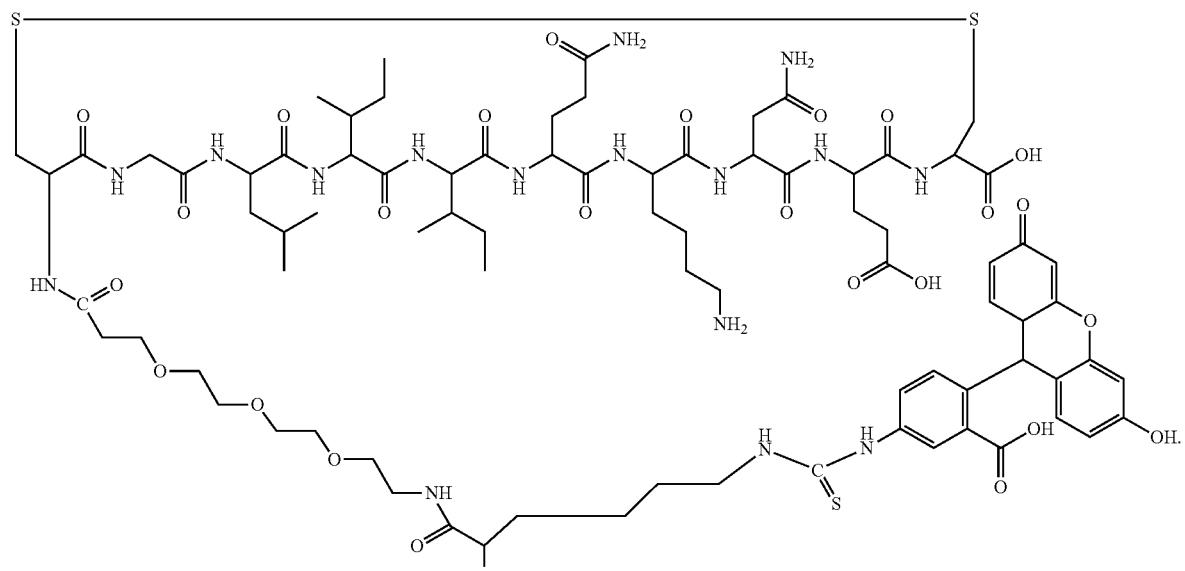

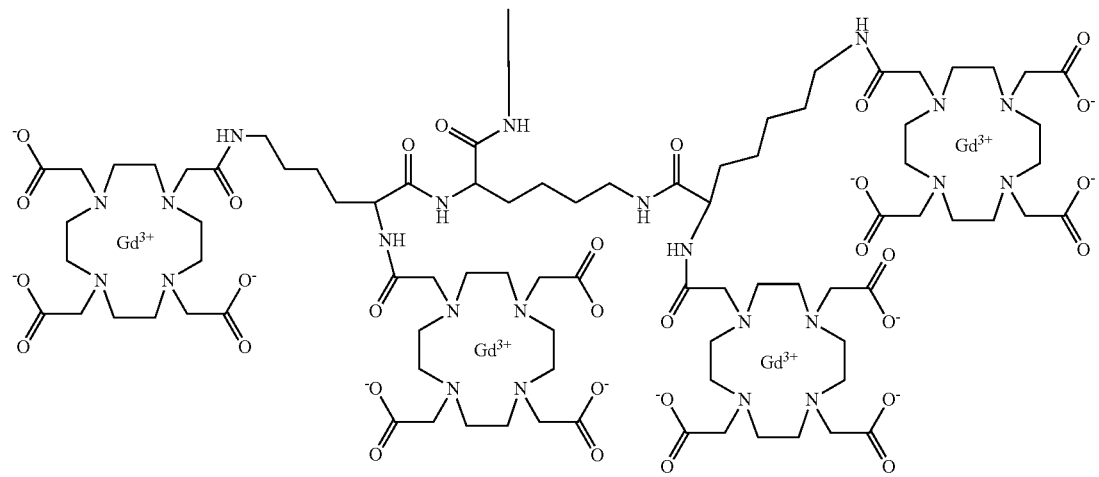

24. The method of claim 22, where the tissue comprises one or more glycoproteins selected from the group consisting of fibronectin, a fibrin-fibronectin complex, and oncofetal fibronectin.

25. A method of imaging a tissue in a subject, comprising:
administering an effective amount of a polypeptide-based contrast agent to the subject;
allowing time for the contrast agent to reach the tissue; and 26. The method of claim 25, wherein the step of imaging the tissue uses a signal selected from the group consisting of an MR signal, a SPECT signal, a ICP-OES signal, a laser light scattering signal, and a PET signal.

27. The method of claim 25, where the tissue comprises one or more glycoproteins selected from the group consisting of fibronectin, a fibrin-fibronectin complex, and oncofetal fibronectin.

28. The compound of claim 1, wherein y has a value of 3 and z has a value of 4.

* * * * *

UNITED STATES PATENT AND TRADEMARK OFFICE
CERTIFICATE OF CORRECTION

| | | |
|---|---|---|
| PATENT NO. | : 9,011,816 B2 | |
| APPLICATION NO. | : 13/071596 | |
| DATED | : April 21, 2015 | |
| INVENTOR(S) | : Zheng-Rong Lu et al. | |

It is certified that error appears in the above-identified patent and that said Letters Patent is hereby corrected as shown below:

In the Claims,

Column 48, line 6, "V" should read --IV--

Signed and Sealed this
Third Day of November, 2015

Michelle K. Lee
*Director of the United States Patent and Trademark Office*